United States Patent
Braun et al.

(10) Patent No.: US 10,035,143 B2
(45) Date of Patent: Jul. 31, 2018

(54) POWDER POLYMER, METHOD FOR THE PREPARATION THEREOF, AND USE AS A THICKENER

(71) Applicant: SOCIETE D'EXPLOITATION DE PRODUITS POUR LES INDUSTRIES CHIMIQUES SEPPIC, Paris (FR)

(72) Inventors: Olivier Braun, St Just St Rambert (FR); Paul Mallo, Le Vesinet (FR)

(73) Assignee: SOCIETE D'EXPLOITATION DE PRODUITS POUR LES INDUSTRIES CHIMQUES SEPPIC, Paris (FR)

( * ) Notice: Subject to any disclaimer, the term of this patent is extended or adjusted under 35 U.S.C. 154(b) by 99 days.

(21) Appl. No.: 14/907,965

(22) PCT Filed: Jul. 18, 2014

(86) PCT No.: PCT/FR2014/051851
§ 371 (c)(1),
(2) Date: Jan. 27, 2016

(87) PCT Pub. No.: WO2015/011380
PCT Pub. Date: Jan. 29, 2015

(65) Prior Publication Data
US 2016/0167040 A1    Jun. 16, 2016

(30) Foreign Application Priority Data

Jul. 24, 2013 (FR) .................................. 13 57280

(51) Int. Cl.
| | |
|---|---|
| *A61Q 19/00* | (2006.01) |
| *B01J 39/20* | (2006.01) |
| *C08F 220/58* | (2006.01) |
| *A61K 8/81* | (2006.01) |
| *C08F 222/10* | (2006.01) |
| *C08F 220/18* | (2006.01) |

(52) U.S. Cl.
CPC ............. *B01J 39/20* (2013.01); *A61K 8/8152* (2013.01); *A61K 8/8158* (2013.01); *A61Q 19/00* (2013.01); *C08F 220/58* (2013.01); *A61K 2800/10* (2013.01); *A61K 2800/48* (2013.01); *A61K 2800/52* (2013.01); *A61K 2800/5424* (2013.01); *C08F 222/1006* (2013.01); *C08F 2220/1883* (2013.01); *C08F 2220/1891* (2013.01)

(58) Field of Classification Search
None
See application file for complete search history.

(56) References Cited

U.S. PATENT DOCUMENTS

| | | | |
|---|---|---|---|
| 2,798,053 | A | 7/1957 | Harold et al. |
| 5,373,044 | A | 12/1994 | Adams et al. |
| 5,422,176 | A | 6/1995 | Schuler et al. |
| 6,197,287 | B1 | 3/2001 | Mallo et al. |
| 6,645,476 | B1 | 11/2003 | Morschhauser et al. |
| 7,771,710 | B2 | 8/2010 | Mallo |
| 8,765,822 | B2 | 7/2014 | Braun et al. |
| 2001/0029287 | A1 | 10/2001 | Loffler et al. |
| 2001/0049419 | A1 | 12/2001 | Mallo et al. |
| 2007/0004851 | A1 | 1/2007 | Zeng |
| 2011/0098364 | A1 | 4/2011 | Braun et al. |
| 2012/0172457 | A1* | 7/2012 | Braun ................. A61K 8/8152 514/772.4 |

FOREIGN PATENT DOCUMENTS

| | | | |
|---|---|---|---|
| EP | 0 301 532 A2 | 2/1989 | |
| EP | 0 503 853 | 9/1992 | |
| EP | 0 562 344 A1 | 9/1993 | |
| EP | 0 750 899 A2 | 1/1997 | |
| EP | 0750899 A2 * | 1/1997 | ............... A61K 8/06 |
| EP | 0 816 403 A2 | 1/1998 | |
| EP | 1 069 142 A1 | 1/2001 | |
| EP | 1 116 733 A1 | 7/2001 | |
| EP | 1 138 703 A1 | 10/2001 | |
| EP | 1 496 081 A1 | 1/2005 | |

(Continued)

OTHER PUBLICATIONS

International Search Report, dated Sep. 4, 2014, from corresponding PCT application.
FR Search Report, dated Feb. 18, 2014, from corresponding FR application.
Japanese Office Action issued in Application No. 2016-528581, dated Feb. 28, 2018 with English Translation.
European Official Action—14 748 247.5—dated May 30, 2018.

*Primary Examiner* — Robert A Wax
*Assistant Examiner* — Melissa S Mercier
(74) *Attorney, Agent, or Firm* — Young & Thompson

(57) ABSTRACT

A cross-linked anionic polyelectrolyte resulting from the polymerization, for 100 mol %: (i) of a proportion no smaller than 30 mol % and smaller than 99.5 mol % monomer units from a monomer having a partially or totally salified strong acid function; (ii) of a proportion no smaller than 0.5 mol % and no greater than 5 mol % monomer units from at least one monomer having Formula (I): $CH_2=CH(CH_3)-C(=O)-OR_1$ (I), wherein Ri is an alkyl radical including 6 to 18 carbon atoms; (iii) of a proportion greater than 0 mol % and no greater than 5 mol % monomer units from at least one diethylene or polyethylene cross-linking monomer; and (iv) optionally, of a proportion smaller than 69.5 mol % monomer units from a neutral monomer. Also, a method for preparing the polyelectrolyte and to the use thereof as a thickener in topical compositions.

8 Claims, No Drawings

(56) References Cited

FOREIGN PATENT DOCUMENTS

| FR | 2 362 872 A1 | 3/1978 |
|----|---|---|
| FR | 2 807 046 A1 | 10/2001 |
| FR | 2 879 607 A1 | 6/2006 |
| JP | 09-136826 A | 5/1997 |
| JP | 09-141080 A | 6/1997 |
| JP | 2001-278921 A | 10/2001 |
| WO | 2004/063228 A1 | 7/2004 |

\* cited by examiner

POWDER POLYMER, METHOD FOR THE PREPARATION THEREOF, AND USE AS A THICKENER

The invention relates to novel thickeners and also to the use thereof in cosmetics and in pharmacy.

The cosmetics industry and the pharmaceutical industry very regularly use synthetic thickening polymers to increase the viscosity of creams, emulsions and various topical solutions. The synthetic thickening polymers currently used in these fields are in two physical forms, the powder form and the liquid form for which the polymer is prepared by inverse emulsion polymerization using surfactants and which is commonly referred to as inverse latex.

The thickening polymers in powder form which are the most well known are polymers based on acrylic acid or copolymers based on acrylic acid and its esters. Mention will be made, for example, of the polymers sold under the trade name Carbopol™ and Pemulen™ and described in particular in American patents 5 373 044 and 2 798 053 and also in European patent EP 0 301 532.

In cosmetics, homopolymers or copolymers based on 2-acrylamido-2-methylpropanesulfonic acid are also used, and always in powder form. These thickening polymers are sold under the trade name Aristoflex™ and described in the European patent applications published under numbers EP 0 816 403, EP 1 116 733 and EP 1 069 142. These thickeners in powder form are obtained by precipitating polymerization: the monomer(s) is (are) dissolved in an organic solvent of benzene, ethyl acetate, cyclohexane or tert-butanol type. This process therefore requires many successive steps of purification of the final product, in order to remove any trace of residual solvent.

The cosmetics industry also very widely uses thickeners in the form of inverse latexes and in particular those sold by the applicant. Mention will be made, for example, of the thickeners Sepigel™ 305, Simulgel™ 600, Simulgel™ EG, Simulgel™ EPG, Simulgel™ NS, Simulgel™ A, Sepiplus™ 400, Sepiplus™ 250 and Sepiplus™ 265. These thickeners are obtained by inverse emulsion polymerization. They have the advantage of being easier to handle and of dispersing very rapidly in water. Furthermore, these products develop notably high thickening performance levels; these performance levels are probably the consequence of the process for preparing them, a dispersed-phase polymerization reaction, which produces very high molecular weight polymers.

Nevertheless, these thickeners in inverse latex form contain an oil and one or more surfactants which can sometimes induce skin intolerance reactions on particularly sensitive subjects; furthermore, this presence of oil makes them unusable for preparing clear gels.

The inventors have therefore developed thickeners which have thickening performance levels equivalent to or greater than inverse latexes, but which are better tolerated by the skin, in particular owing to the absence of any oil phase, which can result in clearer gels. These products are in powder form but have dissolving times, and therefore an ease of use, comparable to those of liquid products. These compounds, described in the European patent application published under number EP 1 496 081, are obtained by conventional polymerization techniques, whether this involves a dispersed-phase polymerization, an inverse suspension polymerization, an inverse emulsion polymerization or an inverse microemulsion polymerization; the thickening systems obtained are then extracted and purified by various techniques, such as precipitation from a third solvent, or precipitation from a third solvent optionally followed by washing, by spray-drying or by azeotropic dehydration, optionally followed by washing with a judiciously chosen solvent. These thickeners therefore combine some of the advantages of conventional powder thickeners (absence of oil, clearer gels obtained) and the advantages of thickeners in inverse latex form (high dissolution rate in oil, notable thickening and stabilizing capacity). However, for certain uses, clients using such thickening systems want to be able to produce gels that are even clearer than those obtained at the current time, or even transparent gels. Furthermore, the gels obtained with these thickeners do not have satisfactory stability when the composition is rich in electrolytes, as is often the case with compositions comprising sunscreens.

The inventors have subsequently sought to develop novel thickening systems which do not have the drawbacks mentioned above and which have sufficient thickening properties so that they are an acceptable alternative to the prior art compositions. This is the subject of the French patent application published under number 2 879 607, the subject of which is in particular an anionic polyelectrolyte which is a linear, branched or crosslinked terpolymer of at least one monomer having a free, partially salified or totally salified strong acid function, with at least one neutral monomer, and at least one monomer of formula (I):

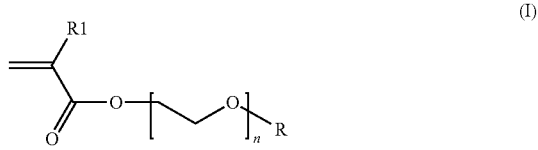

in which R1 represents a hydrogen atom or a methyl radical, R represents a linear or branched alkyl radical comprising from eight to thirty carbon atoms and n represents a number greater than or equal to one and less than or equal to fifty. These polymers have very significant thickening properties, in particular in the presence of electrolytes. In particular, it should be noted that the thickening capacities are barely impacted by the presence of electrolytes. They operate over a wide pH range and make it possible to produce transparent gels. Nevertheless, the applicant demonstrated that the thicknesses of the invention have the drawback of containing one or more monomers containing ethoxylated groups, the use of which in cosmetics is increasingly poorly received.

The European patent application published under number EP 0 562 344 and the French patent application published under number 2 362 872 describe copolymers based in particular on salified 2-acrylamido-2-methyl-1-propanesulfonic acid and on alkyl methacrylate or acrylate, and therefore free of oxyethylenated derivatives. However, these copolymers, even though they are efficient thickeners in water, lose efficiency when not in the presence of salts. They cannot therefore be used in place of the copolymers according to the French patent application published under number 2 879 607.

The European patent application published under number EP 0 750 899 A2 discloses a crosslinked amphiphilic polymer obtained by polymerization of 96.5 mol % of 2-acrylamido-2-methyl-1-propanesulfonic acid, 3.0 mol % of lauryl methacrylate and 0.5 mol % of methylenebis (acrylamide) and the use thereof as an emulsifier or as a solubilizer.

The international application published under number WO 2004/063228 A1 discloses a crosslinked polymer obtained by inverse emulsion polymerization of 39 mol % of 2-acrylamido-2-methyl-1-propanesulfonic acid, 58.6 mol % of acrylic acid, 0.4 mol % of lauryl methacrylate and 2 mol % of methylenebis(acrylamide) and the use thereof as a thickener.

The European patent application published under number EP 1 138 703 A1 discloses polymers obtained by polymerization of from 45 mol % to 97 mol % of partially or totally salified 2-acrylamido-2-methyl-1-propanesulfonic acid, from 3 mol % to 6 mol % of stearyl methacrylate, lauryl methacrylate or hexadecyl acrylate, and optionally from 27 mol % to 52 mol % of acrylamide, alone or as a mixture with 2-hydroxyethyl acrylate, and the use thereof as thickeners.

However, the results in terms of thickening and/or behavior with respect to salts are not satisfactory for these polymers to be selectable as cosmetic formulation thickeners.

The inventors have therefore endeavored to develop a novel anionic polyelectrolyte which, after dispersion at 2% by weight in water, forms a clear gel having a viscosity of at least 30 000 mPa·s measured at 20° C. by means of a Brookfield RVT viscometer at a speed of 5 revolutions per minute, which is stable over a wide pH range and said viscosity of which, measured under the same conditions, is maintained, after the addition of 2% by weight of sodium chloride, at a value at least equal to 50% of its value measured under the same conditions in the absence of salt.

Consequently, according to a first aspect, a subject of the invention is a crosslinked anionic polyelectrolyte resulting from the polymerization, for 100 mol %:
- (i)—of a proportion greater than or equal to 30 mol % and less than 99.5 mol % of monomer units derived from a monomer having a partially salified or totally salified strong acid function;
- (ii)—of a proportion greater than or equal to 0.5 mol % and less than or equal to 5% and more particularly less than or equal to 3% of monomer units derived from at least one monomer of formula (I):

in which $R_1$ represents an alkyl radical comprising from ten to eighteen carbon atoms;
- (iii)—of a proportion greater than 0 mol % and less than or equal to 5 mol % of monomer units derived from at least one diethylene or polyethylene crosslinking monomer;
- (iv)—and of a proportion of less than 69.5 mol % of monomer units derived from a neutral monomer.

The expression "monomer comprising a strong acid function" denotes in particular a monomer comprising the sulfonic acid function or the phosphonic acid function.

In the context of the present invention, the strong acid function is partially or totally salified in the form of an alkali metal salt, such as the sodium salt or of the potassium salt, or in the form of an ammonium salt.

According to one particular aspect, a subject of the invention is an anionic polyelectrolyte as defined above, in which the monomer units derived from the monomer having a partially or totally salified strong acid function are derived from 2-methyl-2-[(1-oxo-2-propenyhamino]-1-propanesulfonic acid partially salified or totally salified in sodium salt or ammonium salt form.

The expression "monomer of formula (I), as defined above," denotes in particular those for which, in said formula (I), $R_1$ represents an alkyl radical comprising ten, twelve, fourteen, sixteen or eighteen carbon atoms.

According to another particular aspect, a subject of the invention is an anionic polyelectrolyte as defined above, in which the monomer units derived from monomers of formula (I):

are derived from lauryl methacrylate of formula ($I_1$), corresponding to formula (I) in which $R_1$ represents a dodecyl radical, and from stearyl methacrylate of formula ($I_2$), corresponding to formula (I) in which $R_1$ represents an octadecyl radical, in a ($I_1$)/($I_2$) mole ratio of greater than or equal to 1/10 and less than or equal to 10/1.

According to another particular aspect, a subject of the invention is an anionic polyelectrolyte as defined above, in which the monomer units derived from monomers of formula (I):

are derived from said lauryl methacrylate of formula ($I_1$) and from isodecyl methacrylate of formula ($I_3$), corresponding to formula (I) in which $R_1$ represents an isodecyl radical, in a ($I_1$)/($I_3$) mole ratio greater than or equal to 1/10 and less than or equal to 10/1.

The term "crosslinked polymer" denotes a nonlinear polymer in the form of a three-dimensional network, which is water-insoluble, but water-swellable and therefore produces a chemical gel.

According to another particular mode, the anionic polyelectrolyte as defined above is characterized in that the mole proportion of monomer units derived from at least one diethylene or polyethylene crosslinking monomer is greater than or equal to 0.1 mol % and less than or equal to 3.0 mol %.

According to another particular mode, the anionic polyelectrolyte as defined above is characterized in that the crosslinking agent and/or the branching agent is chosen from ethylene glycol dimethacrylate, tetraallyloxyethane, ethylene glycol diacrylate, diallylurea, triallylamine, trimethylolpropane triacrylate and methylenebis(acrylamide), or a mixture of these compounds.

When the anionic polyelectrolyte as defined above is obtained by polymerization in the absence of neutral monomer, the mole proportion of monomer with a strong acid function, for 100 mol % of the monomers used, is greater than 97 mol % and is more particularly greater than or equal to 98 mol %.

According to another particular aspect, the anionic polyelectrolyte as defined above is characterized in that it results from a polymerization in the presence of one or more neutral monomers, in which the mole proportion of neutral monomers is, for 100 mol % of the monomers used, less than 69.5 mol % and in that the neutral monomers are chosen from acrylamide, (2-hydroxyethyl) acrylate or N,N-dimethylacrylamide, and more particularly (2-hydroxyethyl) acrylate.

According to another particular aspect, when the anionic polyelectrolyte as defined above is obtained by polymerization in the presence of one or more neutral monomers, the mole proportion of neutral monomer, for 100 mol % of the monomers used, is less than or equal to 30 mol % and is more particularly less than or equal to 20 mol %.

According to another particular mode of the present invention, the anionic polyelectrolyte as defined above comprises, for 100 mol %:
- (i)—a mole proportion greater than or equal to 75 mol % and less than or equal to 95 mol % of monomer units derived from partially salified or totally salified 2-methyl-2-[(1-oxo-2-propenyl)amino]-1-propanesulfonic acid in sodium salt or ammonium salt form;
(ii)—0.5 mol % to 5 mol % of monomer units derived from lauryl methacrylate of formula ($I_1$), and from stearyl methacrylate of formula ($I_2$), in a ($I_1$)/($I_2$) mole ratio greater than or equal to 1/6 and less than or equal to 6/1;
(iii)—a proportion greater than or equal to 0.5 mol % and less than or equal to 3.0 mol % of monomer units derived from at least one diethylene or polyethylene crosslinking monomer chosen from triallylamine, trimethylolpropane triacrylate or methylenebis(acrylamide);
(iv)—and a mole proportion greater than or equal to 4.0 mol % and less than or equal to 20 mol % of monomer units derived from a neutral monomer.

A subject of the invention is more particularly a crosslinked anionic polyelectrolyte as defined above, resulting from the polymerization, for 100 mol %:
(i)—of a proportion greater than or equal to 83 mol % and less than or equal to 90 mol % of monomer units derived from partially salified or totally salified 2-methyl-2-[(1-oxo-2-propenyl)amino]-1-propanesulfonic acid in sodium salt or ammonium salt form;
(ii)—of a proportion greater than or equal to 1.5 mol % and less than or equal to 2.5% of monomer units derived from lauryl methacrylate of formula ($I_1$) and from stearyl methacrylate of formula ($I_2$), in a ($I_1$)/($I_2$) mole ratio greater than or equal to 1/6 and less than or equal to 6/1;
(iii)—of a proportion greater than or equal to 0.5 mol % and less than or equal to 3.0 mol % of monomer units derived from trimethylolpropane triacrylate or methylenebis(acrylamide);
(iv)—of 8 mol % to 15 mol % of monomer units derived from (2-hydroxyethyl) acrylate.

The polyelectrolyte which is the subject of the present invention may also comprise various additives, such as complexing agents, transfer agents or chain limiters.

A subject of the invention is also a process for preparing the polyelectrolyte as defined above, characterized in that it comprises:
a step a) during which all of the monomers, an ammonia-comprising neutralizing agent for the monomer having a strong acid function, the crosslinking agent and, if necessary or if desired, the other monomers and/or additives are mixed in an organic solvent, preferably tert-butanol;
a step b) during which the polymerization reaction is initiated by introducing a free-radical initiator into the dispersion prepared in step a), and then is left to proceed until it is complete;
optionally, a step c) of exchange of the ammonium ion present with the sodium ion or the potassium ion;
a step d) of precipitation of the polymer formed at the end of step b), optionally of step c);
optionally a step e) of drying the precipitate obtained at the end of step d).

As ammonia-comprising neutralizing agent used in step a) of the process as defined above, there is, for example, ammonia or else ammonium hydrogen carbonate.

In step b) of the process as defined above, the polymerization reaction is initiated at a temperature generally greater than or equal to 50° C. using a radical initiator which produces radicals by homolysis, such as dilauroyl peroxide, azobis(isobutyronitrile) or azo derivatives.

According to another embodiment of the process, as defined above, the polymerization reaction is initiated by an oxidizing-reducing pair.

In step c) of the process as defined above, the exchange of the ammonium cation with the sodium cation and with the potassium cation is optionally carried out with sodium tert-butoxide or potassium tert-butoxide.

In step d) of the process as defined above, the precipitation of the polyelectrolyte is carried out either by evaporating off the solvent, or by filtering off the precipitate.

A subject of the invention is also the use of the anionic polyelectrolyte as defined above, as a thickener and/or as a stabilizer and/or as an emulsifier, of a cosmetic, dermopharmaceutical or pharmaceutical topical composition.

The anionic polyelectrolyte according to the invention is more particularly used as an agent for suspending solid particles in cosmetic compositions. These solid particles to be suspended may have various regular or irregular geometries, and may be in the form of beads, balls, rods, flakes, lamellae or polyhedra. These solid particles are characterized by an apparent average diameter of between one micrometer and five millimeters, more particularly between ten micrometers and one millimeter.

Among the solid particles which can be suspended by the polyelectrolyte according to the invention in cosmetic compositions, there are micas, iron oxide, titanium oxide, zinc oxide, aluminum oxide, talc, silica, kaolin, clays, boron nitride, calcium carbonate, magnesium carbonate, magnesium hydrogen carbonate, inorganic colored pigments, polyamides such as nylon-6, polyethylenes, polypropylenes, polystyrenes, polyesters, acrylic or methacrylic polymers such as poly(methyl methacrylate)s, polytetrafluoroethylene, crystalline or microcrystalline waxes, porous spheres, selenium sulfide, zinc pyrithione, starches, alginates, vegetable fibers, Loofah particles, and sponge particles.

In order to optimize its properties of suspending solid particles in cosmetic compositions, the anionic polyelectrolyte according to the invention can be combined with suspending agents commonly used for the preparation of cosmetic compositions, such as low-molecular weight or medium-molecular weight acrylic copolymers.

Finally, a subject of the invention is a topical composition according to the invention usually comprising between 0.1% and 10% by weight and more particularly from 1% to 5% by weight of the anionic polyelectrolyte as defined above. The pH of the topical composition is preferably greater than or equal 3, more particularly greater than or equal to 4.5, and even more particularly greater than or equal to 5.0.

The expression "topical" means that the composition according to the invention is used by application to the skin, the hair, the scalp or the mucus membranes, whether it is a direct application or an indirect application when the topical composition according to the invention is impregnated onto a support intended to be brought into contact with the skin (paper, wipe, textile, transdermal device, etc.).

The topical composition according to the invention may be in any physical form, for example in the form of an aqueous-alcoholic or aqueous-glycolic aqueous gel; a solution; a powder; a suspension, an emulsion, a microemulsion or a nanoemulsion, whether they are of or water-in-oil, oil-in-water, water-in-oil-in-water or oil-in-water-in-oil type.

The topical composition according to the invention may be packaged in a bottle, in a device of pump-"bottle" type, in pressurized form or in an aerosol device, in a device equipped with a perforated wall such as a grid or in a device equipped with a ball applicator (termed "roll-on").

Generally, the topical composition according to the invention also comprises chemical additives normally used in the field of formulations for topical use, such as foaming and/or detergent surfactants, thickening and/or gelling surfactants, thickeners and/or gelling agents, stabilizers, film-forming compounds, solvents and cosolvents, hydrotropic agents, spring or mineral waters, plasticizers, emulsifiers and co-emulsifiers, opacifiers, nacreous agents, overfatting agents, sequestrants, chelating agents, oils, waxes, antioxidants, fragrances, essential oils, preservatives, conditioning agents, deodorants, whitening agents intended for bleaching body hair and the skin, active ingredients intended to provide a treating and/or protective action with respect to the skin or the hair, sunscreens, inorganic fillers or pigments, particles which provide a visual effect or are intended for encapsulating active agents, exfoliant particles, texturing agents, optical brighteners, or insect repellents.

As examples of foaming and/or detergent surfactants, optionally present in the topical composition according to the invention, mention may be made of anionic, cationic, amphoteric or nonionic foaming and/or detergent surfactants.

Among the anionic foaming and/or detergent surfactants that can be used in the topical composition according to the invention, mention may be made of alkali metal salts, alkaline earth metal salts, ammonium salts, amine salts or amino alcohol salts of alkyl ether sulfates, alkyl sulfates, alkylamido ether sulfates, alkylarylpolyether sulfates, monoglyceride sulfates, alpha-olefin sulfonates, paraffin sulfonates, alkyl phosphates, alkyl ether phosphates, alkyl sulfonates, alkylamide sulfonates, alkylaryl sulfonates, alkyl carboxylates, alkyl sulfosuccinates, alkyl ether sulfosuccinates, alkylamide sulfosuccinates, alkyl sulfoacetates, alkylsarcosinates, acylisethionates, N-acyltaurates, acyl lactylates, N-acylated derivatives of amino acids, N-acylated derivatives of peptides, N-acylated derivatives of proteins, or N-acylated derivatives of fatty acids.

Among the amphoteric foaming and/or detergent surfactants that can be used in the topical composition according to the invention, mention may be made of alkyl betaines, alkylamido betaines, sultaines, alkylamidoalkyl sulfobetaines, imidazoline derivatives, phosphobetaines, amphopolyacetates and amphopropionates.

Among the cationic foaming and/or detergent surfactants that can be used in the topical composition according to the invention, mention may particularly be made of quaternary ammonium derivatives.

Among the nonionic foaming and/or detergent surfactants that can be used in the topical composition according to the invention, mention may more particularly be made of alkyl polyglycosides comprising a linear or branched, and saturated or unsaturated aliphatic radical, comprising from 8 to 16 carbon atoms, such as octylpolyglucoside, decylpolyglucoside, undecylenylpolyglucoside, dodecylpolyglucoside, tetradecylpolyglucoside, hexadecylpolyglucoside, 1,12-dodecanediylpolyglucoside; ethoxylated derivatives of hydrogenated castor oil, such as the product sold under the INCI name "Peg-40 hydrogenated castor oil"; polysorbates such as Polysorbate 20, Polysorbate 40, Polysorbate 60, Polysorbate 70, Polysorbate 80 or Polysorbate 85; coconut amides; or N-alkylamines.

In the topical compositions according to the invention also comprising at least one foaming surfactant, the weight ratio between said foaming surfactant and the anionic polyelectrolyte according to the invention is greater than or equal to 1/10 and less than or equal to 40/1, more particularly greater than or equal to 1/1 and less than or equal to 40/1, and even more particularly greater than or equal to 4/1 and less than or equal to 40/1. The combination of at least one foaming surfactant, as defined above, and of the anionic polyelectrolyte according to the invention makes it possible to obtain topical compositions which produce a small volume of foam and in which the air bubbles of which said foam is composed are stable and of sufficiently fine size to limit the risk of eye irritation during application to the face. Such topical compositions according to the invention comprise, for 100% of their weight:

from 0.1% to 5% by weight of the anionic polyelectrolyte according to the invention, from 10% to 50% by weight of at least one foaming surfactant, from 0.01% to 10% by weight of at least one acid agent (A) selected from the group consisting of α-hydroxy acids and β-hydroxy acids, which are free or partially or totally salified, and from 89.89% to 35% of water.

As examples of thickening and/or gelling surfactants optionally present in the topical composition according to the invention, mention may be made of optionally alkoxylated alkyl polyglucoside fatty esters, for instance ethoxylated methylpolyglucoside esters such as PEG 120 methyl glucose trioleate and PEG 120 methyl glucose dioleate sold respectively under the names Glucamate™ LT and Glumate™ DOE120; alkoxylated fatty esters such as PEG 150 pentaerythrytyl tetrastearate sold under the name Crothix™ DS53, PEG 55 propylene glycol oleate sold under the name Antil™ 141; fatty-chain polyalkylene glycol carbamates, for instance PPG-14 laureth isophoryl dicarbamate sold under the name Elfacos™ T211, or PPG-14 palmeth-60 hexyl dicarbamate sold under the name Elfacos™ GT2125.

As examples of thickeners and/or gelling agents optionally present in the topical composition according to the invention, mention may be made of linear or branched or crosslinked polymers of polyelectrolyte type, for instance acrylic acid homopolymer, methacrylic acid homopolymer, 2-methyl-[(1-oxo-2-propenyl)amino]-1-propanesulfonic acid (AMPS) homopolymer, copolymers of acrylic acid and of AMPS, copolymers of acrylamide and of AMPS, copolymers of vinylpyrolidone and of AMPS, copolymers of AMPS and of (2-hydroxyethyl) acrylate, copolymers of AMPS and of (2-hydroxyethyl) methacrylate, copolymers of AMPS and of hydroxyethylacrylamide, copolymers of AMPS and of N,N-dimethylacrylamide, copolymers of AMPS and of tris(hydroxyl-methyl)acrylamidomethane (THAM), copolymers of acrylic or methacrylic acid and of (2-hydroxyethyl) acrylate, copolymers of acrylic or methacrylic acid and of (2-hydroxyethyl) methacrylate, copolymers of acrylic or methacrylic acid and of hydroxyethylacrylamide, copolymers of acrylic or methacrylic acid and of THAM, copolymers of acrylic or methacrylic acid and of N,N-dimethylacrylamide, terpolymers of acrylic or methacrylic acid, of AMPS and of (2-hydroxyethyl) acrylate, terpolymers of acrylic or methacrylic acid, of AMPS and of (2-hydroxyethyl) methacrylate, terpolymers of acrylic or methacrylic acid, of AMPS and of THAM, terpolymers of acrylic or methacrylic acid, of AMPS and of N,N-dimethylacrylamide, terpolymers of acrylic or methacrylic acid, of AMPS and of acrylamide, copolymers of acrylic acid or methacrylic acid and of alkyl acrylates of which the carbon-based chain comprises between four and thirty carbon atoms, and more particularly between ten and thirty carbon atoms, copolymers of AMPS and of alkyl acrylates of which the carbon-based chain comprises between four and thirty carbon atoms and more particularly between ten and thirty carbon atoms. The linear or branched or crosslinked polymers of polyelectrolyte type optionally present in the topical composition according to the invention may be in the form of a solution, an aqueous suspension, a water-in-oil emulsion, an oil-in-water emulsion, or a powder. The linear or branched or crosslinked polymers of polyelectrolyte type optionally present in the topical composition according to the invention can be selected from the products sold under the names Simulgel™ EG, Simulgel™EPG, Sepigel™ 305, Simulgel™ 600, Simulgel™ NS, Simulgel™ INS 100, Simulgel™ FL, Simulgel™ A, Simulgel™ SMS 88, Sepinov™EMT 10, Sepiplus™400, Sepiplus™265, Sepiplus™S, Aristoflex™AVC, Aristoflex™AVS, Novemer™EC-1, Flocare™ET 25, Flocare™ET 75, Flocare™ET 26, Flocare™ET 30, Flocare™ET 58, Flocare™PSD 30, Viscolam™AT 64, Viscolam™AT 100.

As examples of thickeners and/or gelling agents optionally present in the topical composition according to the invention, mention may be made of polysaccharides consisting only of monosaccharides, such as glucans or glucose homopolymers, glucomannoglucans, xyloglycans, galactomannans of which the degree of substitution (DS) of the D-galactose units on the main chain of D-mannose is between 0 and 1, and more particularly between 1 and 0.25, such as galactomannans originating from *cassia* gum (DS=1/5), from locust beam gum (DS=1/4), from tara gum (DS=1/3), from guar gum (DS=1/2) or from fenugreek gum (DS=1).

As examples of thickeners and/or gelling agents optionally present in the topical composition according to the invention, mention may be made of polysaccharides consisting of monosaccharide derivatives, such as sulfated galactans and more particularly carrageenans and agar, uronans and more particularly algins, alginates and pectins, heteropolymers of monosaccharides and of uronic acids and more particularly xanthan gum, gellan gum, exudates of gum Arabic and of karaya gum, and glucosaminoglycans.

In the topical compositions according to the invention also comprising at least one polysaccharide chosen from the group consisting of a galactomannan, gum Arabic and xanthan gum, the weight ratio between said polysaccharide and the anionic polyelectrolyte according to the invention is greater than or equal to 1/3 and less than or equal to 3/1, more particularly or equal to 1/2 and less than or equal to 3/2. The combination of the polysaccharide, as defined above, and of the anionic polyelectrolyte according to the invention makes it possible to obtain topical compositions according to the invention which are in the form of salt-rich emulsions, retaining a high viscosity and a uniform appearance after a prolonged storage period. Such topical compositions according to the invention can comprise, for 100% of their weight, from 0.1% to 25% by weight of at least one salt and can have a dynamic viscosity measured at 20° C., by means of a Brookfield viscometer, of greater than or equal to 30 000 mPa·s and less than or equal to 200 000 mPa·s.

As examples of thickeners and/or gelling agents optionally present in the topical composition according to the invention, mention may be made of cellulose, cellulose derivatives such as methylcellulose, ethylcellulose or hydroxypropylcellulose, silicates, starch, hydrophilic starch derivatives, and polyurethanes.

As examples of stabilizers optionally present in the topical composition according to the invention, mention may be made, for example, of microcrystalline waxes, and more particularly ozokerite, inorganic salts such as sodium chloride or magnesium chloride, and silicone polymers such as polysiloxane polyalkyl polyether copolymers.

As examples of solvents optionally present in the topical composition according to the invention, mention may be made of water, organic solvents such as glycerol, diglycerol, glycerol oligomers, ethylene glycol, propylene glycol, butylene glycol, 1,3-propanediol, 1,2-propanediol, hexylene glycol, diethylene glycol, xylitol, erythritol, sorbitol, water-soluble alcohols such as ethanol, isopropanol or butanol, and mixtures of water and said organic solvents.

As examples of spring or mineral waters optionally present in the topical composition according to the invention, mention may be made of spring or mineral waters having a mineralization of at least 300 mg/l, in particular Avene water, Vittel water, waters from the Vichy basin, Uriage water, Roche Posay water, Bourboule water, Enghien-les-bains water, Saint-Gervais-les bains water, Néris-les-bains water, Allevard-les-bains water, Digne water, Maizieres water, Neyrac-les-bains water, Lons le Saunier water, Rochefort water, Saint Christau water, Fumades water and Tercis-les-bains water.

As examples of hydrotropic agents optionally present in the topical composition according to the invention, mention may be made of the xylene sulfonates, cumene sulfonates, hexylpolyglucoside, 2-ethylhexylpolyglucoside and n-heptylpolyglucoside.

As examples of emulsifying surfactants optionally present in the topical composition according to the invention, mention may be made of nonionic surfactants, anionic surfactants and cationic surfactants.

As examples of nonionic emulsifying surfactants optionally present in the topical composition according to the invention, mention may be made of fatty acid esters of sorbitol, for instance the products sold under the names Montane™40, Montane™60, Montane™70, Montane™80 and Montane™85; compositions comprising glyceryl stearate and steric acid ethoxylated at between 5 mol and 150 mol of ethylene oxide, for instance the composition comprising steric acid ethoxylated at 135 mol of ethylene oxide and glyceryl stearate sold under the name Simulsol™ 165; mannitan esters; ethoxylated mannitan esters; sucrose esters; methylglucoside esters; alkyl polyglycosides comprising a linear or branched and saturated or unsaturated aliphatic radical, comprising from 14 to carbon atoms, such as tetradecylpolyglucoside, hexadecylpolyglucoside, octadecylpolyglucoside, hexadecylpolyxyloside, octadecylpolyxyloside, eicosylpolyglucoside, dodecosylpolyglucoside, 2-octyldodecylpolyxyloside or 12-hydroxystearylpolyglucoside; compositions of linear or branched and saturated or unsaturated fatty alcohols, comprising from 14 to 36 carbon atoms, and of alkyl polyglycosides as described above.

As examples of nonionic surfactants optionally present in the topical composition according to the invention mention may be made of glyceryl stearate citrate, cetearyl sulfate, soaps such as sodium stearate or triethanolammonium stearate, and salified N-acylated amino acid derivatives, for instance stearoyl glutamate.

As examples of cationic emulsifier surfactants optionally present in the topical composition according to the invention, mention may be made of amine oxides, quaternium-82 and the surfactants described in patent application WO 96/00719 and mainly those in which the fatty chain comprises at least 16 carbon atoms.

As examples of opacifiers and/or nacreous agents optionally present in the topical composition according to the invention, mention may be made of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate, and fatty alcohols comprising from 12 to 22 carbon atoms.

As examples of texturing agents optionally present in the topical composition according to the invention, mention may be made of N-acylated derivatives of amino acids, such as the lauroyl lysine sold under the name Aminohope™LL, the octenyl starch succinate sold under the name Dryflo™, the myristyl polyglucoside sold under the name Montanov™ 14, cellulose fibers, cotton fibers, chitosan fibers, talc, sericite and mica.

As examples of deodorants optionally present in the topical composition according to the invention, mention may be made, for example, of alkali metal silicates, zinc salts such as zinc sulfate, zinc gluconate, zinc chloride or zinc lactate; quaternary ammonium salts such as cetyltrimethylammonium salts, cetylpyridinium salts; glycerol derivatives such as glyceryl caprate, glyceryl caprylate, polyglyceryl caprate; 1,2-decanediol; 1,3-propanediol; salicylic acid; sodium bicarbonate; cyclodextrins; metal zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octochlorohydrate, aluminum sulfate, sodium aluminum lactate, complexes of aluminum chlorohydrate and glycol, such as the complex of aluminum chlorohydrate and of propylene glycol, the complex of aluminum dichlorohydrate and of propylene glycol, the complex of aluminum sesquichlorohydrate and of propylene glycol, the complex of aluminum chlorohydrate and of polyethylene glycol, the complex of aluminum dichlorohydrate and of polyethylene glycol, and the complex of aluminum sesquichlorohydrate and of polyethylene glycol.

As examples of oils optionally present in the topical composition according to the invention, mention may be made of mineral oils such as paraffin, liquid petroleum jelly, isoparaffins or white mineral oils; oils of animal origin, such as squalene or squalane; vegetable oils, such as phytosqualane, sweet almond oil, coconut oil, castor oil, jojoba oil, olive oil, rapeseed oil, peanut oil, sunflower oil, wheatgerm oil, corn germ oil, soybean oil, cottonseed oil, alfafa oil, poppyseed oil, pumpkin oil, evening primrose oil, millet oil, barley oil, rye oil, safflower oil, candlenut oil, passion flower oil, hazelnut oil, palm oil, shea butter, apricot kernel oil, beauty leaf oil, sysymbrium oil, avocado oil, calendula oil, oils derived from flowers or from vegetables, ethoxylated vegetable oils; synthetic oils, for instance fatty acid esters such as butyl myristate, propyl myristate, isopropyl myristate, cetyl myristate, isopropyl palmitate, octyl palmitate, butyl stearate, hexadecyl stearate, isopropyl stearate, octyl stearate, isocetyl stearate, dodecyl oleate, hexyl laurate, propylene glycol dicaprylate, lanolic acid-derived esters, such as isopropyl lanolate, isocetyl lanolate, fatty acid monoglycerides, diglycerides and triglycerides, for instance glyceryl triheptanoate, alkyl benzoates, hydrogenated oils, poly(alpha-olefin)s, polyolefins, for instance poly(isobutane), synthetic isoalkanes, for instance isohexadecane, isododecane, perfluoro oils; silicone oils, for instance dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups. The term "oils" is intended to mean, in the present application, compounds and/or mixtures of compounds which are insoluble in water and which have a liquid aspect at a temperature of 25° C.

As examples of waxes optionally present in the topical composition according to the invention, mention may be made of beeswax, carnauba wax, candelilla wax, ouricury wax, Japan wax, cork fiber wax, sugarcane wax, paraffin waxes, lignite waxes, microcrystalline waxes, lanolin wax; ozokerite; polyethylene wax; silicone waxes; vegetable waxes; fatty alcohols and fatty acids which are solid at ambient temperature; glycerides which are solid at ambient temperature. The term "waxes" is intended to mean, in the present application, compounds and/or mixtures of compounds which are insoluble in water and which have a solid aspect at a temperature greater than or equal to 45° C.

As examples of active ingredients optionally present in the topical composition according to the invention, mention may be made of vitamins and derivatives thereof, in particular esters thereof, such as retinol (vitamin A) and esters thereof (retinyl palmitate for example), ascorbic acid (vitamin C) and esters thereof, sugar derivatives of ascorbic acid (for instance ascorbyl glucoside), tocopherol (vitamin E) and esters thereof (for instance tocopheryl acetate), vitamin B3 or B10 (niacinamide and derivatives thereof); compounds showing a skin-lightening or -depigmenteding action, for instance the ω-undecelynoyl phenylalanine sold under the name Sepiwhite™MSH, Sepicalm™VG, the glycerol monoester and/or diester of ω-undecelynoyl phenylalanine, ω-undecelynoyl dipeptides, arbutin, kojic acid, hydroquinone; compounds showing a soothing action, in particular Sepicalm™ S, allantoin and bisabolol; anti-inflammatories; compounds showing a moisturizing action, such as urea, hydroxyureas, glycerol, polyglycerols, glycerolglucoside, diglycerolglucoside, polyglycerylglucosides, xylitylglucoside; polyphenol-rich plant extracts, for instance grape extracts, pine extracts, wine extracts, olive extracts; compounds showing a slimming or lipolytic action, for instance caffeine or derivatives thereof, Adiposlim™, Adipoless™, fucoxanthine; N-acylated proteins; N-acylated peptides, for instance Matrixil™; N-acylated amino acids; partial hydrolyzates of N-acylated proteins; amino acids; peptides; total protein hydrolyzates; soybean extracts, for example Raffermine™; wheat extracts, for example Tensine™ or Gliadine™; plant extracts, such as tannin-rich plant extracts, isoflavone-rich plant extracts or terpene-rich plant extracts; extracts of freshwater or seawater algae; marine plant extracts; marine extracts in general, such as corals; essential waxes; bacterial extracts; ceramides; phospholipids; compound showing an antimicrobial action or a purifying action, for instance Lipacide™ CBG, Lipacide™ UG, Sepicontrol™ A5; Octopirox™ or Sensiva™ SC50; compounds showing an energizing or stimulating property, for instance Physiogenyl™, panthenol and derivatives thereof, for instance Sepicap™ MP; anti-aging active agents, for instance Sepilift™ DPHP, Lipacide™ PVB, Sepivinol™, Sepivital™ Manoliva™, Phyto-Age™, Timecode™; Survicode™; anti-photoaging active agents; agents for protecting the integrity of the dermoepidermal junction; agents for increasing the synthesis of extracellular matrix components such as collagen, elastins, glycosaminoglycans; active agents which act favorably on chemical cell communication, for instance cytokines, or physical cell communication, for instance integrins; active agents which create a "heating" sensation on the skin, for instance skin microcirculation activators (for instance nicotinic acid derivatives) or products which create a feeling of "freshness" on the skin (for instance menthol and derivatives); active agents for improving skin microcirculation, for example veinotonics; draining active agents; active agents for decongestive purposes, for instance extracts of *ginko biloba*, of ivy, of horse chestnut, of bamboo, of ruscus, of butcher's broom, of *Centella asiatica*, of fucus, of rosemary, of willow; agents for tanning or browning the skin, for instance dihydroxyacetone, isatin, alloxane, ninhydrin, glyceraldehyde, mesotartic aldehyde, glutaraldehyde, erythrulose.

As examples of antioxidants optionally present in the topical composition according to the invention, mention may be made of EDTA and salts thereof, citric acid, tartaric acid, oxalic acid, BHA (butylhydroxyanisol), BHT (butylhydroxytoluene), tocopherol derivatives such as tocopheryl acetate, mixtures of antioxidant compounds such as Dissolvine™ GL 47S sold by the company Akzo Nobel under the INCI name: Tetrasodium Glutamate Diacetate.

As examples of sunscreens optionally present in the topical composition according to the invention, mention may be made of those which appear in the modified cosmetics directive 76/768/EEC annex VII. Among the organic sunscreens optionally present in the topical composition according to the invention, mention may be made of the family of benzoic acid derivatives, for instance para-aminobenzoic acids (PABAs), in particular monoglyceryl esters of PABA, ethyl esters of N,N-propoxy PABA, ethyl esters of N,N-diethoxy PABA, ethyl esters of N,N-dimethyl-PABA, methyl esters of N,N-dimethyl-PABA, butyl esters of N,N-dimethyl-PABA; the family of anthranilic acid derivatives, for instance homomenthyl-N-acetyl anthranilate; the family of salicylic acid derivatives, for instance amyl salicylate, homomenthyl salicylate, ethylhexyl salicylate, phenyl salicylate, benzyl salicylate, or p-isopropylphenyl salicylate; the family of cinnamic acid derivatives, for instance ethylhexyl cinnamate, ethyl-4-isopropyl cinnamate, methyl 2,5-diisopropyl-cinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, mono(2-ethylhexanoyl)glyceryl di(para-methoxycinnamate); the family of benzophenone derivatives, for instance 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octyloxybenzophenone, 4-hydroxy-3-carboxybenzophenone; 3-(4'-methylbenzylidene)-d,l-camphor, 3-(benzylidene)-d,l-camphor, camphor benzalkonium methosulfate; urocanic acid, ethyl urocanate; the family of sulfonic acid derivatives, for instance 2-phenylbenzimidazole-5 sulfonic acid and salts thereof; the family of triazine derivatives, for instance hydroxyphenyl triazine, ethylhexyloxyhydroxyphenyl-4-methoxyphenyltriazine, 2,4,6-trianillino-(p-carbo-2'-ethylhexyl-1'-oxy)-1,3,5-triazine, benzoic acid 4,4-((6-(((1,1-dimethylethyl)amino) carbonyl)phenyl)amino)-1,3,5-triazine-2,4-diyl diimino) bis (2-ethylhexyl) ester, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methyphenyl) benzotriazole; dibenzazine; dianisoylmethane, 4-methoxy-4"-t-butylbenzoylmethane; 5-(3,3-dimethyl-2-norbornylidene)-3-pentan-2-one; the family of diphenyl acrylate derivatives, for instance 2-ethylhexyl-2-cyano-3,3-diphenyl-2-propenoate, ethyl-2-cyano-3,3-diphenyl-2-propenoate; the family of polysiloxanes, for instance benzylidene siloxane malonate.

Among the inorganic sunscreens, also known as "inorganic screens", optionally present in the topical composition according to the invention, mention may be made of titanium oxide, zinc oxide, cerium oxide, zirconium oxide, yellow, red or black iron oxides, and chromium oxides. These inorganic screens may or may not be micronized, may or may not have undergone surface treatments and may be optionally present in the form of aqueous or oil predispersions.

The topical composition according to the invention may be more particularly a fragrancing composition, having a translucent or transparent or whitish appearance, which is stable with respect to storage over time and which does not impair the olfactory properties of the fragrances used, comprising, for 100% of their weight:

from 0.1% to 40% by weight, more particularly from 0.1% to 20% by weight, more particularly from 1% to 12% by weight, and even more particularly from 1% to 10% by weight of at least one fragrancing or aromatizing substance, from 5% to 90% by weight, more particularly from 20% to 70% by weight of at least one volatile solvent, from 0.1% to 5% by weight, more particularly from 0.1% to 3.5% by weight, and more particularly from 0.5% to 3% by weight, and even more particularly between 0.8% and 2% by weight of at least one anionic polyelectrolyte according to the invention, from 94.8% to 5% by weight of water, optionally, from 2% to 20% by weight of at least one oil and/or one wax, as defined above.

The term "fragrancing or aromatizing substance" denotes a substance of natural or synthetic origin capable of giving off a more or less persistent odor.

The topical composition according to the invention may be more particularly a suspension of solid particles, comprising, for 100% of its weight:

from 0.1% to 5% by weight, more particularly from 0.15% to 2.5% by weight of at least one anionic polyelectrolyte according to the invention, from 0.05% to 2% by weight, more particularly from 0.15% to 2.5% by weight of at least one solid particle.

The suspended solid particles present in the topical composition according to the invention are previously described in the present application. Depending on the nature of the solid particles, the topical composition according to the invention comprising said solid particles in suspension can be used as a gel for exfoliating bodily skin and facial skin, or as an anti-aging care gel for the skin when the suspended particles are microspheres comprising moisturizing cosmetic active agents, for instance microspheres comprising hyaluronic acid.

The topical composition according to the invention may be more particularly a makeup composition intended to be applied to the skin, to the eyelashes or to the nails, for instance a foundation composition, a mascara composition, or an eyeshadow composition. The use of the polyelectrolyte according to the invention for preparing a mascara composition according to the invention makes it possible to more easily remove the mascara from the eyelashes during makeup removal.

The following examples illustrate the invention without, however, limiting it.

EXAMPLE 1 (ACCORDING TO THE INVENTION)

Crosslinked polyelectrolyte of ammonium 2-methyl-2-[(1-oxo-2-propenyl)amino]-1-propanesulfonate, of (2-hydroxyethyl) acrylate, or stearyl methacrylate and of lauryl methacrylate, crosslinked with trimethylolpropane triacrylate (ATBS/HEA/SMA/LAUMA: 88.1/9.9/1.5/0.5; polyelectrolyte 1)

The following are charged to a reactor maintained at 25° C., with stirring, containing 245 g of tert-butanol:
- 33.8 g of 2-acrylamido-2-methylpropanesulfonic acid (ATBS);
- 12.9 g of ammonium hydrogen carbonate;
- 2.12 g of (2-hydroxyethyl) acrylate (HEA);
- 0.93 g of stearyl methacrylate (SMA);
- 0.24 g of lauryl methacrylate (LAUMA);
- 0.54 g of trimethylolpropane triacrylate (TMPTA).

After a period of time sufficient to achieve good homogenization of the solution, deoxygenation is carried out by nitrogen sparging and then the temperature of the medium is brought to 70° C. When the desired temperature is reached, 0.50 g of dilauroyl peroxide is added. The polymerization begins instantaneously. The reaction medium is then maintained at this temperature for approximately 60 minutes, then heated to 80° C. This temperature is maintained for 2 hours before cooling. The powder which formed during polymerization is filtered off and dried so as to obtain polyelectrolyte 1.

EXAMPLE 2 (ACCORDING TO THE INVENTION)

Crosslinked polyelectrolyte of ammonium -methyl-2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 88.1/9.9/1.0/1.0; polyelectrolyte 2)

The following are charged to a reactor maintained at 25° C., with stirring, containing 245 g of tert-butanol:
- 33.8 g of 2-acrylamido-2-methylpropanesulfonic acid (ATBS);
- 12.9 g of ammonium hydrogen carbonate;
- 2.12 g of (2-hydroxyethyl) acrylate (HEA);
- 0.62 g of stearyl methacrylate (SMA);
- 0.48 g of lauryl methacrylate (LAUMA);
- 0.54 g of trimethylolpropane triacrylate (TMPTA).

After a period of time sufficient to achieve good homogenization of the solution, deoxygenation is carried out by nitrogen sparging and then the temperature of the medium is brought to 70° C. When the desired temperature is reached, 0.50 g of dilauroyl peroxide is added. The polymerization begins instantaneously. The reaction medium is then maintained at this temperature for approximately 60 minutes, then heated to 80° C. This temperature is maintained for 2 hours before cooling. The powder which formed during polymerization is filtered off and dried so as to obtain polyelectrolyte 2.

EXAMPLE 3 (ACCORDING TO THE INVENTION)

Crosslinked polyelectrolyte of ammonium 2-methyl-2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 88.1/9.9/0.7/1.3; polyelectrolyte 3)

The following are charged to a reactor maintained at 25° C., with stirring, containing 245 g of tert-butanol:
- 33.8 g of 2-acrylamido-2-methylpropanesulfonic acid (ATBS);
- 12.9 g of ammonium hydrogen carbonate;
- 2.12 g of (2-hydroxyethyl) acrylate (HEA);
- 0.46 g of stearyl methacrylate (SMA);
- 0.60 g of lauryl methacrylate (LAUMA);
- 0.54 g of trimethylolpropane triacrylate (TMPTA).

After a period of time sufficient to achieve good homogenization of the solution, deoxygenation is carried out by nitrogen sparging and then the temperature of the medium is brought to 70° C. When the desired temperature is reached, 0.50 g of dilauroyl peroxide is added. The polymerization begins instantaneously. The reaction medium is then maintained at this temperature for approximately 60 minutes, then heated to 80° C. This temperature is maintained for 2 hours before cooling. The powder which formed during polymerization is filtered off and dried so as to obtain polyelectrolyte 3.

EXAMPLE 4 (ACCORDING TO THE INVENTION)

Crosslinked polyelectrolyte of ammonium 2-methyl-2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 88.1/9.9/0.3/1.7; polyelectrolyte 4)

The following are charged to a reactor maintained at 25° C., with stirring, containing 245 g of tert-butanol:
- 33.8 g of 2-acrylamido-2-methylpropanesulfonic acid (ATBS);
- 12.9 g of ammonium hydrogen carbonate;
- 2.12 g of (2-hydroxyethyl) acrylate (HEA);
- 0.19 g of stearyl methacrylate (SMA);
- 0.82 g of lauryl methacrylate (LAUMA);
- 0.54 g of trimethylolpropane triacrylate (TMPTA).

After a period of time sufficient to achieve good homogenization of the solution, deoxygenation is carried out by nitrogen sparging and then the temperature of the medium is brought to 70° C. When the desired temperature is reached, 0.50 g of dilauroyl peroxide is added. The polymerization begins instantaneously. The reaction medium is then maintained at this temperature for approximately 60 minutes, then heated to 80° C. This temperature is maintained for 2 hours before cooling. The powder which formed during polymerization is filtered off and dried so as to obtain polyelectrolyte 4.

EXAMPLE 5 (ACCORDING TO THE INVENTION)

Crosslinked polyelectrolyte of ammonium 2-methyl-2-[(1-oxo-2-propenyl)amino]-1-propane-sulfonate, of (2-hydroxyethyl) acrylate, of stearyl methacrylate and of lauryl methacrylate, crosslinked with trimethylolpropane triacrylate (ATBS/HEA/SMA/LAUMA: 86.4/9.7/1.9/2.0; polyelectrolyte 5)

The following are charged to a reactor maintained at 25° C., with stirring, containing 245 g of tert-butanol:
- 33.8 g of 2-acrylamido-2-methylpropanesulfonic acid (ATBS);
- 12.9 g of ammonium hydrogen carbonate;
- 2.12 g of (2-hydroxyethyl) acrylate (HEA);
- 1.24 g of stearyl methacrylate (SMA);
- 0.96 g of lauryl methacrylate (LAUMA);
- 0.54 g of trimethylolpropane triacrylate (TMPTA).

After a period of time sufficient to achieve good homogenization of the solution, deoxygenation is carried out by nitrogen sparging and then the temperature of the medium is brought to 70° C. When the desired temperature is reached, 0.50 g of dilauroyl peroxide is added. The polymerization begins instantaneously. The reaction medium is then maintained at this temperature for approximately 60 minutes, then heated to 80° C. This temperature is maintained for 2 hours before cooling. The powder which formed during polymerization is filtered off and dried so as to obtain polyelectrolyte 5.

EXAMPLE 6 (ACCORDING TO THE INVENTION)

Crosslinked polyelectrolyte of ammonium 2-methyl-2-[(1-oxo-2-propenyl)amino]-1-propane-sulfonate, of (2-hydroxyethyl) acrylate and of stearyl methacrylate, crosslinked with trimethylolpopane triacrylate (ATBS/HEA/SMA: 88.2/9.8/2; polyelectrolyte 6)

The following are charged to a reactor maintained at 25° C., with stirring, containing 245 g of tert-butanol:
- 33.8 g of 2-acrylamido-2-methylpropanesulfonic acid (ATBS);
- 12.9 g of ammonium hydrogen carbonate;
- 2.12 g of (2-hydroxyethyl) acrylate (HEA);
- 1.24 g of stearyl methacrylate (SMA);
- 0.54 g of trimethylolpropane triacrylate (TMPTA).

After a period of time sufficient to achieve good homogenization of the solution, deoxygenation is carried out by nitrogen sparging and then the temperature of the medium is brought to 70° C. When the desired temperature is reached, 0.50 g of dilauroyl peroxide is added. The polymerization begins instantaneously. The reaction medium is then maintained at this temperature for approximately 60 minutes, and then heated to 80° C. This temperature is maintained for 2 hours before cooling. The powder which formed during polymerization is filtered off and dried so as to obtain polyelectrolyte 6.

EXAMPLE 7 (ACCORDING TO THE INVENTION)

Crosslinked polyelectrolyte of ammonium 2-methyl-2-[(1-oxo-2-propenyl)amino]-1-propane-sulfonate, of (2-hydroxyethyl) acrylate, and of lauryl methacrylate, crosslinked with trimethylolpropane triacrylate (ATBS/HEA/LAUMA: 88.1/9.9/2.0; polyelectrolyte 7)

The following are charged to a reactor maintained at 25° C., with stirring, containing 245 g of tert-butanol:
- 33.8 g of 2-acrylamido-2-methylpropanesulfonic acid (ATBS);
- 12.9 g of ammonium hydrogen carbonate;
- 2.12 g of (2-hydroxyethyl) acrylate (HEA);
- 0.96 g of lauryl methacrylate (LAUMA);
- 0.54 g of trimethylolpropane triacrylate (TMPTA).

After a period of time sufficient to achieve good homogenization of the solution, deoxygenation is carried out by nitrogen sparging and then the temperature of the medium is brought to 70° C. When the desired temperature is reached, 0.50 g of dilauroyl peroxide is added. The polymerization begins instantaneously. The reaction medium is then maintained at this temperature for approximately 60 minutes, and then heated to 80° C. This temperature is maintained for 2 hours before cooling. The powder which formed during polymerization is filtered off and dried so as to obtain polyelectrolyte 7.

EXAMPLE 8 (ACCORDING TO THE INVENTION)

Crosslinked polyelectrolyte of sodium 2-methyl 2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 88.1/9.9/1.0/1.0; polyelectrolyte 8)

The following are charged to a reactor maintained at 25° C., with stirring, containing 245 g of tert-butanol:
- 33.8 g of 2-acrylamido-2-methylpropanesulfonic acid (ATBS);
- 12.9 g of ammonium hydrogen carbonate;
- 2.12 g of (2-hydroxyethyl) acrylate (HEA);
- 0.62 g of stearyl methacrylate (SMA);
- 0.48 g of lauryl methacrylate (LAUMA);
- 0.54 g of trimethylolpropane triacrylate (TMPTA).

After a period of time sufficient to achieve good homogenization of the solution, deoxygenation is carried out by nitrogen sparging and then the temperature of the medium is brought to 70° C. When the desired temperature is reached, 0.50 g of dilauroyl peroxide is added. The polymerization begins instantaneously. The reaction medium is then maintained at this temperature for approximately 60 minutes and then heated to 80° C. This temperature is maintained for 2 hours. Sodium tert-butoxide is then added so as to exchange the ammonium ions with sodium ions, followed by cooling. The powder which formed during polymerization is filtered off and dried so as to obtain polyelectrolyte 8.

EXAMPLE 9 (ACCORDING TO THE INVENTION)

Crosslinked polyelectrolyte of ammonium 2-methyl-2-[(1-oxo-2-propenyl)amino]-1-propanesulfonate, of (2-hydroxyethyl) acrylate, of isodecyl methacrylate and of lauryl methacrylate, crosslinked with trimethylolpropane triacrylate (polyelectrolyte 9)

The following are charged to a reactor maintained at 25° C., with stirring, containing 245 g of tert-butanol:

33.8 g of 2-acrylamido-2-methylpropanesulfonic acid (ATBS);
12.9 g of ammonium hydrogen carbonate;
2.12 g of (2-hydroxyethyl) acrylate (HEA);
0.41 g of isodecyl methacrylate (IDMA);
0.48 g of lauryl methacrylate (LAUMA);
0.54 g of trimethylolpropane triacrylate (TMPTA).

After a period of time sufficient to achieve good homogenization in the solution, deoxygenation was carried out by nitrogen sparging and then temperature of the medium was brought to 70° C. When the desired temperature was reached, 0.50 g of dilauroyl peroxide is added. The polymerization begins instantaneously. The reaction medium is then maintained at this temperature for approximately 60 minutes, and then heated to 80° C. This temperature is maintained for 2 hours before cooling. The powder which formed during polymerization is filtered off and dried so as to obtain polyelectrolyte 9.

The following examples were prepared by carrying out the process in a manner similar to the previous examples.

EXAMPLE 10 (ACCORDING TO THE INVENTION)

Crosslinked polyelectrolyte of sodium 2-methyl-2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 94/4/1/1; polyelectrolyte 10).

EXAMPLE 11 (ACCORDING TO THE INVENTION)

Crosslinked polyelectrolyte of sodium 2-methyl-2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 83/15/1/1; polyelectrolyte 11).

EXAMPLE 12 (ACCORDING TO THE INVENTION)

Crosslinked polyelectrolyte of sodium 2-methyl-2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 88.2/9.8/1/1; polyelectrolyte 12).

EXAMPLE 13 (ACCORDING TO THE INVENTION)

Crosslinked polyelectrolyte of sodium 2-methyl-2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 88/9.6/1.2/1.2; polyelectrolyte 13).

EXAMPLE 14 (ACCORDING TO THE INVENTION)

Crosslinked polyelectrolyte of sodium 2-methyl-2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 82.5/14.5/1.5/1.5; polyelectrolyte 14).

EXAMPLE 15 (ACCORDING TO THE INVENTION)

Crosslinked polyelectrolyte of sodium 2-methyl-2-[(1-oxo-2-propenyl)amino]-1-propanesulfonate, of (2-hydroxyethyl) acrylate, of stearyl methacrylate and of lauryl methacrylate, crosslinked with trimethylolpropane triacrylate (ATBS/HEA/SMA/LAUMA: 89/10/0.5/0.5; polyelectrolyte 15).

B) Thickening Properties:

The thickeners according to the invention were evaluated as follows:

a)—viscosity measurement ($\mu$):

at 2% by weight in water, and at 2% by weight in water and comprising 2% of sodium chloride.

These viscosity measurements, expressed in mPas, were carried out at 25° C. by means of a Brookfield RVT rheometer equipped with the number 6 spindle and set at a rotational speed of 5 revolutions per minute (rpm). The measurements were carried out just after preparation of the aqueous dispersion. The results are recorded in the following table:

|  | Viscosity at 2% in water | Viscosity at 2% in water comprising 2% of sodium chloride | $\Delta\mu = (\mu_1 - \mu_0)/\mu_0$ |
|---|---|---|---|
| Polyelectrolyte 1 | $\mu_0$ = 55 800 mPas | $\mu_1$ = 32 400 mPas | −42% |
| Polyelectrolyte 2 | $\mu_0$ = 42 600 mPas | $\mu_1$ = 27 400 mPas | −36% |
| Polyelectrolyte 3 | $\mu_0$ = 45 400 mPas | $\mu_1$ = 31 800 mPas | −30% |
| Polyelectrolyte 4 | $\mu_0$ = 36 000 mPas | $\mu_1$ = 32 200 mPas | −11% |
| Polyelectrolyte 5 | $\mu_0$ = 60 000 mPas | $\mu_1$ = 15 200 mPas | −75% |
| Polyelectrolyte 6 | $\mu_0$ = 55 400 mPas | $\mu_1$ = 26 000 mPas | −53% |
| Polyelectrolyte 7 | $\mu_0$ = 24 600 mPas | $\mu_1$ = 21 600 mPas | −12% |
| Polyelectrolyte 8 | $\mu_0$ = 44 600 mPas | $\mu_1$ = 28 000 mPas | −37% |
| Polyelectrolyte 10 | $\mu_0$ = 40 600 mPas | $\mu_1$ = 37 000 mPas | −9% |
| Polyelectrolyte 11 | $\mu_0$ = 43 000 mPas | $\mu_1$ = 45 2000 mPas | +5% |
| Polyelectrolyte 12 | $\mu_0$ = 44 000 mPas | $\mu_1$ = 39 200 mPas | −11% |
| Polyelectrolyte 13 | $\mu_0$ = 44 800 mPas | $\mu_1$ = 35 800 mPas | −20% |
| Polyelectrolyte 14 | $\mu_0$ = 45 400 mPas | $\mu_1$ = 31 200 mPas | −31% |
| Polyelectrolyte 15 | $\mu_0$ = 41 400 mPas | $\mu_1$ = 29 200 mPas | −29% |

These results reveal that the polymers according to the invention are thickening polymers. Among these, polymers 1, 2, 3, 4 and 8 to 15 are more particularly suitable for use in cosmetic formulations, their aqueous dispersion exhibiting a decrease of less than 50% in their viscosity in the presence of salts, while having a pronounced thickening nature in water (>30 000 mPas).

C) Examples of Formulations Prepared with the Polyelectrolytes According to the Invention (Proportions Expressed as Percentages by Weight)

EXAMPLE 1

Care Cream

CYCLOMETHICONE™: 10%
Polyelectrolyte 1: 0.8%
MONTANOV™ 68: 2%
Stearyl alcohol: 1%
Stearic alcohol: 0.5%
Preservative: 0.65%
Lysine: 0.025%
EDTA (disodium salt): 0.05%
Xanthan gum: 0.2%
Glycerol: 3%
Water: qs 100%

EXAMPLE 2

Aftershave Balm

Formula
A Polyelecctrolyte 2: 1.5%
　Water: qs 100%
B MICROPEARL™ M 100: 5.0%
　SEPICIDE™ CI: 0.50%
　Fragrance: 0.20%
　95° ethanol: 10.0%
PROCEDURE: Add B to A.

EXAMPLE 3

Satin Emulsion for the Body

Formula
A SIMULSOL™ 165: 5.0%
　LANOL™ 1688: 8.50%
　Shea butter: 2%
　Liquid paraffin: 6.5%
　LANOL™ 14M: 3%
　LANOL™ S: 0.6%
B Water: 66.2%
C MICROPEARL™ M 100: 5%
D Polyelectrolyte 3: 3%
E SEPICIDE™ CI: 0.3%
　SEPICIDE™ HB: 0.5%
　AQUAXYL™: 3%
　Fragrance: 0.20%
　Vitamin E acetate: 0.20%
　Sodium pyrolidinonecarboxylate: 1%
PROCEDURE: Add C to B, emulsify B in A at 70° C., then add D at 60° C. and then E at 30° C.

EXAMPLE 4

O/W Cream

Formula
A SIMULSOL™ 165: 5.0%
　LANOL™ 1688: 20.0%
　LANOL™ P: 1.0%
B Water: qs 100%
C Polyelectrolyte 4: 2.50%
D SEPICIDE™ CI: 0.20%
　SEPICIDE™ HB: 0.30%
PROCEDURE: Introduce B into A at around 75° C.; add C at around 60° C., then D at around 45° C.

EXAMPLE 5

Nonfatty Antisun Gel

Formula
A Polyelectrolyte 8: 3.00%
　Water: 30%
B SEPICIDE™ CI: 0.20%
　SEPICIDE™ HB: 0.30%
　Fragrance: 0.10%
C Dye: qs
　Water: 30%
D MICROPEARL™ M100: 3.00%
　Water: qs 100%
E Silicone oil: 2.0%
　PARSOL™ MCX: 5.00%
PROCEDURE: Introduce B into A; add C, then D, then E.

EXAMPLE 6

Antisun Milk

Formula
A MONTANOV™ S: 3.0%
　Sesame oil: 5.0%
　PARSOL™ MCX: 5.0%
　Carrageenan λ: 0.10%
B Water: qs 100%
C Polyelectrolyte 3: 0.80%
D Fragrance: qs
　Preservative: qs
PROCEDURE: Emulsify B and A at 75° C. then add C at around 60° C., then D at around 30° C. and adjust the pH if necessary.

EXAMPLE 7

Massage Gel

Formula
A Polyelectrolyte 2: 3.5%
　Water: 20.0%
B Dye: 2 drops/100 g
　Water: qs
C Ethanol: 10%
　Menthol: 0.10%
D Silicone oil: 5.0%
PROCEDURE: Add B to A, then add C followed by D to the mixture.

EXAMPLE 8

Moisturizing and Matting Foundation

Formula
A Water: 20.0%
　Butylene glycol: 4.0%
　PEG-400: 4.0%

PECOSIL™ PS100: 1.0%
Sodium hydroxide: qs pH=9
Titanium dioxide: 7.0%
Talc: 2.0%
Yellow iron oxide: 0.8%
Red iron oxide: 0.3%
Black iron oxide: 0.05%
B LANOL™ 99: 8%
Caprylic capric triglyceride 8%
MONTANOV™ 202: 5.00%
C Water: qs 100%
MICROPEARL™ M305: 2.0%
Tetrasodium EDTA: 0.05%
D CYCLOMETHICONE™: 4.0%
Xanthan gum: 0.2%
Polyelectrolyte 1: 0.8%
E SEPICIDE™ HB: 0.5%
SEPICIDE CI: 0.3%
Fragrance: 0.2%
PROCEDURE: Prepare, at 80° C., the mixtures B+D and A+C, then mix and emulsify together.

EXAMPLE 9

Radiance Gel

Formula
A Polyelectrolyte 4: 4%
Water: 30%
B ELASTIN HPM™: 5.0%
C MICROPEARL™ M100: 3%
Water: 5%
D SEPICIDE™ CI: 0.2%
SEPICIDE™ HB: 0.3%
Fragrance: 0.06%
50% Sodium pyrolidinonecarboxylate: 1%
Water: qs 100%
PROCEDURE: Prepare A; add B, then C, then D.

EXAMPLE 10

Body Milk

MONTANOV™ S: 3.5%
LANOL™ 37T: 8.0%
SOLAGUM™ L: 0.05%
Water: qs 100%
Benzophenone-3: 2.0%
DIMETHICONE™ 350 cPs: 0.05%
Polyelectrolyte 3: 0.8%
Preservative: 0.2%
Fragrance: 0.4%

EXAMPLE 11

Makeup-Removing Emulsion Comprising Sweet Almond Oil

MONTANOV™ 68: 5%
Sweet almond oil: 5%
Water: qs 100%
Polyelectrolyte 8: 0.3%
Glycerol: 5%
Preservative: 0.2%
Fragrance: 0.3%

EXAMPLE 12

Moisturizing Cream for Greasy Skin

MONTANOV™ 68: 5%
Cetyl stearyl octanoate: 8%
Octyl palmitate: 2%
Water: qs 100%
Polyelectrolyte 1: 0.6%
MICROPEARL™ M100: 3.0%
Mucopolysaccharides: 5%
SEPICIDE™ HB: 0.8%
Fragrance: 0.3%

EXAMPLE 13

Alcohol-Free Soothing Aftershave Balm

LIPACIDE™ PVB: 1.0%
LANOL™ 99: 2.0%
Sweet almond oil: 0.5%
Polyelectrolyte 4: 3.5%
Water: qs 100%
Fragrance: 0.4%
SEPICIDE™ HB: 0.4%
SEPICIDE™ CI: 0.2%

EXAMPLE 14

Cream Comprising AHAs for Sensitive Skin

Mixture of N-lauroyl amino acids: 0.1% to 5%
Magnesium potassium aspartate: 0.002% to 0.5%
LANOL™ 99: 2%
MONTANOV™ 68: 5.0%
Water: qs 100%
Polyelectrolyte 2: 1.50%
Gluconic acid: 1.50%
Triethanolamine (TEA): 0.9%
SEPICIDE™ HB: 0.3%
SEPICIDE™ CI: 0.2%
Fragrance: 0.4%

EXAMPLE 15

Soothing after-Sun Care Product

Mixture of N-lauroyl amino acids: 0.1% to 5%
Magnesium potassium aspartate: 0.002% to 0.5%
LANOL™ 99: 10.0%
Water: qs 100%
Polyelectrolyte 3: 2.50%
SEPICIDE™ HB: 0.3%
SEPICIDE™ CI: 0.2%
Fragrance: 0.4%
Dye: 0.03%

EXAMPLE 16

Makeup-Removing Milk

MONTANOV™ S: 3%
PRIMOL™ 352: 8.0%
Sweet almond oil: 2%

Water: qs 100%
Polyelectrolyte 2: 0.8%
Preservative: 0.2%

EXAMPLE 17

Fluid Emulsion Having an Alkaline pH

MARCOL™ 82: 5.0%
Sodium hydroxide: 10.0%
Water: qs 100%
Polyelectrolyte 1: 1.5%

EXAMPLE 18

Fluid Foundation

SIMULSOL™ 165: 5.0%
LANOL™ 84D: 8.0%
LANOL™ 99: 5.0%
Water: qs 100%
Mineral pigments and fillers: 10.0%
Polyelectrolyte 4: 1.2%
Preservative: 0.2%
Fragrance: 0.4%

EXAMPLE 19

Antisun Milk

MONTANOV™ S: 3.5%
LANOL™ 37T: 10.0%
PARSOL™ MCX: 5.0%
EUSOLEX™ 4360: 2.0%
Water: qs 100%
Polyelectrolyte 8: 1.8%
Preservative: 0.2%
Fragrance: 0.4%

EXAMPLE 20

Gel for the Area Around the Eyes

Polyelectrolyte 1: 2.0%
Fragrance: 0.06%
Sodium pyrolidinonecarboxylate: 0.2%
DOW CORNING™ 245 Fluid: 2.0%
Water: qs 100%

EXAMPLE 21

Leave-on Care Composition

Polyelectrolyte 8: 1.5%
Fragrance: qs
Preservative: qs
DOW CORNING™ X2 8360: 5.0%
DOW CORNING™ Q2 1401: 15.0%
Water: qs 100%

EXAMPLE 22

Slimming Gel

Polyelectrolyte 4: 5%
Ethanol: 30%
Menthol: 0.1%
Caffeine: 2.5%
Ruscus extract: 2%
Ivey extract: 2%
SEPICIDE™ HB: 1%
Water: qs 100%

EXAMPLE 23

Ultra Natural Tinted Cream Gel

Formula
A Water: 10.0%
  Butylene glycol: 4.0%
  PEG-400: 4.0%
  PECOSIL™ PS100: 1.5%
  Sodium hydroxide: qs pH=7
  Titanium dioxide: 2.0%
  Yellow iron oxide: 0.8%
  Red iron oxide: 0.3%
  Black iron oxide: 0.05%
B LANOL™ 99: 4.0%
  Caprylic capric triglyceride: 4.0%
  SEPIFEEL™ ONE: 1.0%
  Polyelectrolyte 3: 3.0%
C Water: qs 100%
  MICROPEARL™ M305: 2.0%
  Tetrasodium EDTA: 0.05%
  CYCLOMETHICONE™: 4.0%
D SEPICIDE™ HB: 0.5%
  SEPICIDE™ CI: 0.3%
  Fragrance: 0.2%
PROCEDURE: Prepare the mixture B+C and then add A then D.

EXAMPLE 24

Care Product for Greasy Skin

MICROPEARL™ M310: 1.0%
Polyelectrolyte 2: 5.0%
Octyl isononanoate: 4.0%
Water: qs 100%
SEPICONTROL™ A5: 4.0%
Fragrance: 0.1%
SEPICIDE™ HB: 0.3%
SEPICIDE™ CI: 0.2%
CAPIGEL™ 98: 0.5%
Water: 10%

EXAMPLE 25

Cream Comprising AHAs

MONTANOV™ 68: 5.0%
LIPACIDE™ PVB: 1.05%
LANOL™ 99: 10.0%
Water: qs 100%
Gluconic acid: 1.5%
Triethanolamine: 0.9%
Polyelectrolyte 1: 1.5%

Fragrance: 0.4%
SEPICIDE™ HB: 0.2%
SEPICIDE™ CI: 0.4%

EXAMPLE 26

Non-Greasy Self-Tanning Product for the Face and Body

LANOL™ 2681: 3.0%
Polyelectrolyte 8: 2.5%
Water: qs 100%
Dihydroxy acetone: 3.0%
Fragrance: 0.2%
SEPICIDE™ HB: 0.8%
Sodium hydroxide: qs pH=5

EXAMPLE 27

Antisun Milk Comprising Tahiti Monoi

Tahiti monoi: 10%
LIPACIDE™ PVB: 0.5%
Polyelectrolyte 4: 2.2%
Water: qs 100%
Fragrance: 0.1%
SEPICIDE™ HB: 0.3%
SEPICIDE™ CI: 0.1%
PARSOL™ MCX: 4.0%

EXAMPLE 28

Antisun Care Product for the Face

CYCLOMETHICONE™ and DIMETHICONOL™: 4.0%
Polyelectrolyte 3: 3.5%
Water: qs 100%
Fragrance: 0.1%
SEPICIDE™ HB: 0.3%
SEPICIDE™ CI: 0.21%
PARSOL™ MCX: 5.0%
Titanium oxide-coated mica: 2.0%
Lactic acid: qs pH=6.5

EXAMPLE 29

Sun-Free Tannin Emulsion

LANOL™ 99: 15%
MONTANOV™ 68: 5.0%
PARSOL™ MCX: 3.0%
Water: qs 100%
Dihydroxyacetone: 5.0%
Monosodium phosphate: 0.2%
Polyelectrolyte 2: 0.5%
Fragrance: 0.3%
SEPICIDE™ HB: 0.8%
Sodium hydroxide: qs pH=5.

EXAMPLE 30

Care Cream

CYCLOMETHICONE™: 10%
Polyelectrolyte 4: 0.8%
MONTANOV™ 68: 4.5%
Preservative: 0.65%
Lysine: 0.025%
EDTA (disodium salt): 0.05%
Xanthan gum: 0.2%
Glycerol: 3%
Water: qs 100%

EXAMPLE 31

Care Cream

CYCLOMETHICONE™: 10%
Polyelectrolyte 3: 0.8%
MONTANOV™ 68: 4.5%
Perfluoropolymethyl isopropyl ether: 0.5%
Preservative: 0.65%
Lysine: 0.025%
EDTA (disodium salt): 0.05%
PEMULEN™ TR1: 0.2%
Glycerol: 3%
Water: qs 100%

EXAMPLE 32

Body Milk

Formula
A SIMULSOL™ 165: 5.0%
   LANOL™ 1688: 12.0%
   LANOL™ 14M: 2.0%
   Cetyl alcohol: 0.3%
   SCHERCEMOL™ OP: 3%
B Water: qs 100%
C Polyelectrolyte 2: 0.35%
D SEPICIDE™ CI: 0.2%
   SEPICIDE™ HB: 0.5%
   Fragrance: 0.20%
PROCEDURE: Emulsify B in A at around 75° C.; add C at around 60° C., then D at around 30° C.

EXAMPLE 33

Massage Care Gel

Formula
A Polyelectrolyte 1: 3.00%
   Water: 30%
B SEPICIDE™ CI: 0.20%
   SEPICIDE™ HB: 0.30%
   Fragrance: 0.05%
C Dye: qs
   Water: qs 100%
D MICROPEARL™ SQL: 5.0%
   LANOL™ 1688: 2%
PROCEDURE: Prepare A; add B, then C, then D.

EXAMPLE 34

Body Milk

Formula
A MONTANOV™ S: 3.0%
   Glyceryl triheptonate: 10.0%
B Water: qs 100%

C Polyelectrolyte 8: 1.0%
D Fragrance: qs
Preservative: qs
PROCEDURE: Melt A at approximately 75° C. Emulsify B and A at 75° C. then add C at around 60° C., then D.

EXAMPLE 35

Alcohol-Free Soothing Aftershave Balm

Mixture of lauroyl amino acids: 0.1% to 5%
Magnesium potassium aspartate: 0.02% to 0.5%
LANOL™ 99: 2%
Sweet almond oil: 0.5%
Water: qs 100%
Polyelectrolyte 2: 3%
SEPICIDE™ HB: 0.3%
SEPICIDE™ CI: 0.2%
Fragrance: 0.4%

EXAMPLE 36

Body Milk

MONTANOV™ S: 3.5%
LANOL™ 37T: 8.0%
SOLAGUM™ L: 0.05%
Water: qs 100%
Benzophenone-3: 2.0%
DIMETHICONE™ 350 cPs: 0.05%
Polyelectrolyte 4: 0.8%
Preservative: 0.2%
Fragrance: 0.4%

EXAMPLE 37

Alcohol-Free Soothing Aftershave Balm

LIPACIDE™ PVB: 1.0%
LANOL™ 99: 2.0%
Sweet almond oil: 0.5%
Polyelectrolyte 1: 3.5%
Water: qs 100%
Fragrance: 0.4%
SEPICIDE™ HB: 0.4%
SEPICIDE™ CI: 0.2%

EXAMPLE 38

Refreshing Aftershave Gel

LIPACIDE™ PVB: 0.5%
LANOL™ 99: 5.0%
Polyelectrolyte 1: 2.5%
Water: qs 100%
MICROPEARL™ LM: 0.5%
Fragrance: 0.2%
SEPICIDE™ HB: 0.3%
SEPICIDE™ CI: 0.2%

EXAMPLE 39

Cream Comprising AHAs

MONTANOV™ 68: 5.0%
LIPACIDE™ PVB: 1.05%
LANOL™ 99: 10.0%
Water: qs 100%
Gluconic acid: 1.5%
Triethanolamine: 0.9%
Polyelectrolyte 4: 1.5%
Fragrance: 0.4%
SEPICIDE™ HB: 0.2%
SEPICIDE™ CI: 0.4%

EXAMPLE 40

Sheen Gel

Polyelectrolyte 2: 1.5%
Volatile silicone: 25%
Monopropylene glycol: 25%
Demineralized water: 10%
Glycerol: qs 100%

EXAMPLE 41

Slimming Gel

Polyelectrolyte 3: 1.5%
Isononyl isononanoate: 2%
Caffeine: 5%
Ethanol: 40%
MICROPEARL™ LM: 2%
Demineralized water: qs 100%
Preservative, fragrance: qs

EXAMPLE 42

Makeup-Removing Milk

SIMULSOL™ 165: 4%
MONTANOV™ 202: 1%
Caprylate caprate triglyceride: 15%
PECOSIL™ DCT: 1%
Demineralized water: qs
CAPIGEL™ 98: 0.5%
Polyelectrolyte 15: 1%
PROTEOL™ APL: 2%
Sodium hydroxide: qs pH=7

EXAMPLE 43

Rinse-Off Restructuring Cream Mask for Stressed and Embrittled Hair

KETROL™T: 0.5%
PECOSIL™ SPP50: 0.75%
N-cocoyl amino acids: 0.70%
Butylene glycol: 3.0%
Polyelectrolyte 4: 3.0%
MONTANOV™ 82: 3.0%
Jojoba oil: 1.0%
LANOL™ P: 6.0%
AMONYL™ DM: 1.0%
LANOL™ 99: 5.0%
SEPICIDE™ HB: 0.3%
SEPICIDE™CI: 0.2%
Fragrance: 0.2%
Water: qs 100%

EXAMPLE 44

Antisun Cream

SIMULSOL™ 165: 3%
MONTANOV™ 202: 2%

C12-C15 Benzoate: 8%
PECOSIL™ PS 100: 2%
DIMETHICONE™: 2%
CYCLOMETHICONE™: 5%
Octyl para-methoxycinnamate: 6%
Benzophenone-3: 4%
Titanium oxide: 8%
Xanthan gum: 0.2%
Butylene glycol: 5%
Demineralized water: qs 100%
Polyelectrolyte 1: 1.5%
Preservative, fragrance: qs

EXAMPLE 45

Combination Skin Care Gel

Polyelectrolyte 4: 4%
Plant squalane: 5%
DIMETHICONE: 1.5%
SEPICONTROL™ A5: 4%
Xanthan gum: 0.3%
Water: qs 100%
Preservative, fragrance: qs

EXAMPLE 46

Hair Lotion

Butylene glycol: 3.0%
Polyelectrolyte 2: 3%
SIMULSOL™1293: 3.0%
Lactic acid: qs pH=6
SEPICIDE™ HB: 0.2%
SEPICIDE™CI: 0.3%
Fragrance: 0.3%
Water: qs 100%

EXAMPLE 47

Protective and Relaxing Shampoo

AMONYL™ 675 SB: 5.0%
Sodium lauroyl ether sulfate at 28%: 35.0%
Polyelectrolyte 4: 3.0%
SEPICIDE™ HB: 0.5%
SEPICIDE™CI: 0.3%
Sodium hydroxide: qs pH=7.2
Fragrance: 0.3%
Dye (FDC blue 1/yellow 5): qs
Water: qs 100%

EXAMPLE 48

Leave-on Protector; Antistress Care Product for Hair

KETROL™T: 0.5%
Mixture of cocoyl amino acids: 3.0%
Butylene glycol: 5.0%
DC 1501: 5.0%
Polyelectrolyte 4: 4.0%
SEPICIDE™ HB: 0.5%
SEPICIDE™CI: 0.3%
Fragrance: 0.3%
Water: qs 100%

EXAMPLE 49

Vitamin-Comprising Cream

SIMULSOL™ 165: 5%
MONTANOV™ 202: 1%
Caprylic/capric triglycerides: 20%
Vitamin A palmitate: 0.2%
Vitamin E acetate: 1%
MICROPEARL™ M305: 1.5%
Polyelectrolyte 3: 2%
Water: qs 100%
Preservative, fragrance: qs

EXAMPLE 50

Antisun Gel

Polyelectrolyte 8: 3.00%
SEPICIDE™ CI: 0.20%
SEPICIDE™ HB: 0.30%
Fragrance: 0.10%
Dye: qs
Silica: 3.00%
Water: qs 100%
Silicone oil: 2.0%
Benzophenone-3: 5.00%

EXAMPLE 51

Lip Gloss

Polyelectrolyte 3: 1.50%
SCHERCEMOL™ TISC: 15.00%
VISTANOL™ NPGC: 15.00%
CANDURIN PAPRIKA™: 0.50%
MONTANOX™ 80: 1.00%
ANTARON™ V216: 0.90%
Apricot flavor: 0.20%
SEPICIDE™ HB: 0.50%
C MALTIDEX™ H16322: qs 100%

EXAMPLE 52

Sun Soil Pressed Powder

Polyelectrolyte 1: 2.00%
LANOL™ 99: 12.00%
SEPIWHITE™ MSH: 1.00%
Talc: 33.00%
MICROPEARL™ M310: 3.00%
Yellow iron oxide: 0.80%
Red iron oxide: 0.30%
Black iron oxide: 0.05%
Mica: qs 100%

EXAMPLE 53

Emulsion for Atopic-Prone Skin

ARLACEL™ P135: 2.00%
Polyelectrolyte 4: 1.00%
LANOL™1688: 14.00%
PRIMOL™ 352: 8.00%
Glycerol: 5.00%

EXAMPLE 54

Soothing Antisun Care Product (Water-in-Silicone)

Polyelectrolyte 2: 2.00%
DC5225C: 20.00%
DC345: 10.00%
SEPICALM™ VG: 3.00%
Titanium dioxide MT100T: 5.00%
Zinc oxide Z-cote HP1: 5.00%
SEPICIDE™ HB: 0.30%
Fragrance: 0.05%
SEPICIDE™ CI: 0.20%
Glycerol: 5.00%
Sodium chloride: 2.00%
Water: qs 100%

Water: qs 100%
Magnesium sulfate: 0.70%
SEPICIDE™ HB: 0.30%
SEPICIDE™ CI: 0.20%
MICROPEARL™ M310: 5.00%

EXAMPLE 55

Multiphase Care Product

Polyelectrolyte 4: 3.00%
C12-15 alkyl benzoate: 25.00%
AQUAXYL™: 3.00%
SEPITONIC™ M3: 1.00%
SEPICIDE™ HB: 0.50%
SEPICIDE™ CI: 0.30%

EXAMPLE 56

Self-Tanning Gel

Ethanol: 30%
Dihydroxyacetone: 5%
Menthol: 0.1%
Caffeine: 2.5%
Ivry extract: 2%
SEPICIDE™ HB: 1%
Water: qs 100%

EXAMPLE 57

Antisun and Self-Tanning Gel

MONTANOV™ S: 3.0%
Glyceryl triheptanoate: 10.0%
LIPACIDE™ PVB: 1.05%
Polyelectrolyte 2: 2.2%
Water: qs 100%
Dihydroxyacetone: 5%
Fragrance: 0.1%
SEPICIDE™ HB: 0.3%
SEPICIDE™ CI: 0.1%
PARSOL™ MCX: 4.0%

EXAMPLE 58

Self-Tanning Cream Comprising α-Hydroxy Acids

MONTANOV™ 68: 5.0%
LIPACIDE™ PVB: 1.05%
LANOL™ 99: 10.0%
Water: qs 100%
Gluconic acid: 1.5%
Dihydroxyacetone: 3%
Triethanolamine: 0.9%
Polyelectrolyte 1: 1.5%
Fragrance: 0.4%
SEPICIDE™ HB: 0.2%
SEPICIDE™ CI: 0.4%

EXAMPLE 59

Self-Tanning Cream Comprising α-Hydroxy Acids for Sensitive Skin

Mixture of N-lauroyl amino acids: 0.1% to 5%
Magnesium potassium aspartate: 0.002% to 0.5%
MONTANOV™ 68: 5.0%
LANOL™ 99: 2.0%
Water: qs 100%
Lactic acid: 1.5%
Dihydroxyacetone: 3.5%
Triethanolamine: 0.9%
Polyelectrolyte 2: 1.5%
Fragrance: 0.4%
SEPICIDE™ HB: 0.3%
SEPICIDE™ CI: 0.2%

EXAMPLE 60

Self-Tanning Moisturizing Satin Emulsion

SIMULSOL™ 165: 5.0%
LANOL™ 1688: 8.5%
Galam butter: 2%
Liquid paraffin: 6.5%
LANOL™ 14M: 3%
LANOL™ S: 0.6%
Water: 66.2%
Dihydroxyacetone: 3%
MICROPEARL™ M100: 5%
Polyelectrolyte 3: 3%
AQUAXYL™: 5%
Vitamin E acetate: 0.20%
Sodium pyrolidinonecarboxylate: 0.20%
Fragrance: 0.2%
SEPICIDE™ HB: 0.5%
SEPICIDE™ CI: 0.3%

EXAMPLE 61

Organo-Mineral Antisun Spray

Formula
A Isodecyl neopentanoate: 20%
  CYCLODIMETHICONE™: 5%
  Ethylhexyl methoxycinnamate: 6%
  Butylmethoxydibenzoylmethane: 3%
  DL alpha-tocopherol: 0.05%
B Water: qs 100%
  Tetrasodium EDTA: 0.2%
  Glycerol: 7%
  Phenylbenzimidazole sulfonic acid (salified with required molar amount of sodium hydroxide): 3%

C Polyelectrolyte 8: 1.3%
  KETROL™CG-T: 0.315%
  EFFICACIA™M: 0.385%
D SEPICIDE™ HB: 1%
  Fragrance: 0.1%

EXAMPLE 62

Body Cream

Formula:
  Triglycerides 4555 (C8C10): 12%
  C12-C15 alkyl benzoate: 5.3%
  Isohexadecane: 2.7%
  Cetyl alcohol: 2%
  DL alpha-tocopherol: 0.10%
  Polyelectrolyte 2: 1.5%
  Tara gum: 0.5%
  Water: qs 100%
  GIVOBIO™ GZn: 1%
  SEPICALM™S: 3%
  EUXYL™ PE910: 1%
  Fragrance: 0.1%

EXAMPLE 63

Invigorating Fragrancing Gel

A Polyelectrolyte 3: 2.25%
  Aqua/Water: qs 100%
B Lemon essential oil: 0.50%
  Sage essential oil: 0.50%
  Glycerol: 2.00%
  Ethanol: 83.00%

EXAMPLE 64

UV Protective Fragranced Hair Gel

A Polyelectrolyte 4: 1.00%
  SOLAGUM™ AX: 1.00%
  Disodium EDTA: 0.05%
  Aqua/Water: qs 100%
  Dye: qs
B Disodium phenylbenzimidazole tetrasulfonate: 5.00%
  Benzophenone-4: 3.00%
  Aminomethyl propanol: 4.00%
  Aqua/Water: 25.00%
C Fragrance concentrate A: 0.10%
  Phenoxyethanol and ethylhexyl glycerol: 1.00%
  Polysorbate 20: 0.50%
  PEG/PPG-20/15 DIMETHICONE™: 1.00%
  Ethanol: 20.00%
D Triethanolamine: qs pH=7-7.2

EXAMPLE 65

Gelled Eau De Cologne

A Polyelectrolyte 10: 3.00%
  Aqua/Water: qs 100%
B Fragrance concentrate B: 4.00%
  Ethanol: 81.00%

EXAMPLE 66

Styling Gel

Polyelectrolyte 4: 2.00%
Polyvinylpyrrolidone: 2.00%
VP/methacrylamide/n-vinylimidazole copolymer 15%
Ethanol: 20%
Polysorbate 20: 2.5%
Fragrance: 0.3%
DIMETHICONE COPOLYOL™: 1.0%
Water: qs 100%

EXAMPLE 67

Fragrancing Water-in-Oil Emulsion

A Isononyl isononanoate: 6%
  Ethylhexyl glycerol: 1%
B EASYNOV™ 2.5%
C Polyelectrolyte 12: 0.5%
  AQUAXYL™: 3%
  Water: qs 100%
D Ethanol: 40%
  Fragrance: 2.0%

EXAMPLE 68

Antiperspirant Water-in-Oil Emulsion

A Isononyl isononanoate: 6%
  Ethylhexyl glycerol: 1%
B EASYNOV™ 2.5%
C Polyelectrolyte 8: 0.5%
  AQUAXYL™: 3%
  Water: qs 100%
  Aluminum hydrochloride (50%): 30%

EXAMPLE 69

Lightening Water-in-Oil Emulsion

A Isononyl isononanoate: 6%
  Fragrance: 0.1%
  Phenoxyethanol & ethylhexyl glycerol: 1%
B EASYNOV™: 1.5%
  Polyelectrolyte 2: 0.5%
  SEPIWHITE™MSH: 2%
  Water: qs 100%

EXAMPLE 70

Sulfate-Free Shower Gel

AMONYL™ 380 BA (28.9% AM): 10.4%
ORAMIX™NS10 ((54.2% AM) 22.73%
Water: qs 100%
Lactic acid in solution at 45%: 0.3%
Polyelectrolyte 1: 2%

EXAMPLE 71

Shower Gel

AMONYL™ 380 BA (28.9% AM): 10.4%
Sodium lauryl ether (2.2 EO) sulfate (27.1% AM) 44.3%
Water qs 100%
Lactic acid in solution at 45% 0.3%
Polyelectrolyte 3 0.8%

EXAMPLE 72

Shampoo

A JAGUAR™ C14 S: 0.20%
  Water: qs 100%
  Polyelectrolyte 2: 0.20%
B Disodium EDTA: 0.05%
C 70% sodium lauryl ether sulfate: 16.0%
  AMONYL™ 380 BA: 3.0%
  ORAMIX™ NS10: 4.0%
  Glycol distearate: 1.5%
  Cetearyl alcohol: 0.5%
  Coconut ethanol amide: 0.8%
  Coconut diethanol amide: 0.8%
D Polyquaternium-7: 2.0%
  Dimethicone & Laureth-23 & Laureth-3: 1.0%
  Dimethiconol & TEA-Dodecyl benzenesulfonate: 2.0%
  SEPICIDE™ HB: 1.0%
  Fragrance: 0.3%
  Sodium chloride: 0.8%
  Citric acid (25%): qs pH=6.0

EXAMPLE 73

2-in-1 Shampoo

A JAGUAR™C14 S: 0.2%
  Water: qs 100%
  Polyelectrolyte 1: 0.2%
B Disodium EDTA: 0.05%
C 70% sodium lauryl ether sulfate: 16.0%
  AMONYL™ 380 BA: 3.0%
  ORAMIX™ NS10 4.0%
  Glycol distearate: 1.5%
  Cetearyl alcohol: 0.5%
  Coconut ethanol amide 0.8%
  Coconut diethanol amide 0.8%
D Polyquaternium-7 1.8%
  Polyquaternium-10 0.2%
  Dimethicone & Laureth-23 & Laureth-3 1.0%
  Dimethiconol & TEA-Dodecyl benzenesulfonate 2.0%
  SEPICIDE™ HB: 1.0%
  Fragrance: 0.3%
  Sodium chloride: 0.8%
  Citric acid (25%): qs pH=6.0

EXAMPLE 74

Anti-Frizziness Disentangling Spray

A MONTANOV™ L: 0.5%
  Cyclopentasiloxane and dimethiconol: 2.0%
B Polyelectrolyte 2: 1.2%
  Water: qs 60%
C Water: qs 100%
  Cetrimonium chloride: 0.5%
D SEPICIDE™ HB: 1.0%
  Fragrance: 0.1%
  Lactic acid: qs pH=6.0

The commercial products used in the examples are defined as follows:

SIMULSOL™ 1293 is hydrogenated and ethoxylated castor oil, with an ethoxylation index equal to 40, sold by the company SEPPIC;
CAPIGEL™ 98 is an acrylate copolymer-based liquid thickener sold by the company SEPPIC;
KELTROL™CG-T and KETROL™ T are xanthan gum sold by the company CP KELCO;
LANOL™ 99 is isononyl isononanoate sold by the company SEPPIC;
DC 1501 ™ is a mixture of cyclopentasiloxane and dimethiconol sold by the company DOW CHEMICAL;
MONTANOV™ 82 is an emulsifier based on cetearyl alcohol and cocoyl glucoside;
MONTANOV™ 68 (cetearyl glucoside) is a self-emulsifiable composition as described in WO 92/06778, sold by the company SEPPIC;
MICROPEARL™ M100 is an ultrafine powder with a very soft feel and a matting action, sold by the company MATSUMO;
SEPICIDE™ CI, imidazolidinyl urea, is a preservative sold by the company SEPPIC;
PEMULEN™ TR1 is an acrylic polymer sold by GOODRICH;
SIMULSOL™ 165 is self-emulsifiable glyceryl stearate sold by the company SEPPIC;
LANOL™ 1688 is an emollient ester with a nongrease effect, sold by the company SEPPIC;
LANOL™ 14M and LANOL™ S are consistency factors sold by the company SEPPIC;
SEPICIDET™ HB (INCI name: phenoxyethanol/methylparaben/ethyl-paraben/propylparaben/butylparaben) is a preservative sold by the company SEPPIC;
AQUAXYL™ (INCI name: xylityl glucoside and anhydroxylitol and xylitol): moisturizing composition sold by the company SEPPIC;
SCHERCEMOL™ OP is an emollient ester with a nongreasy effect;
LANOL™ P is an additive with a stabilizing effect, sold by the company SEPPIC;
PARSOL™ MCX is octyl para-methoxycinnamate, sold by the company GIVAUDAN;
MONTANOV™ S is a nacreous agent, sold by the company SEPPIC, based on a mixture of alkyl polyglucosides such as those described in WO 95/13863;
MICROPEARL™ SQL is a mixture of microparticles containing squalane which is released by the action of massaging; it is sold by the company MATSUMO;
LANOL™ 37T is glyceryl triheptanoate, sold by the company SEPPIC;
SOLAGUM™ L is a carrageenan sold by the company SEPPIC;
MARCOL™ 82 is a liquid paraffin sold by the company EXXON;
LANOL™ 84D is dioctyl malate sold by the company SEPPIC;
PARSOL™ NOX is a sunscreen sold by the company GIVAUDAN;
EUSOLEX™ 4360 is a sunscreen sold by the company MERCK;
DOW CORNING™ 245 (or DC 245™) fluid is CYCLOMETHICONE, sold by the company DOW CORNING;
LIPACIDE™ PVB, is an acylated wheat protein hydrolyzate sold by the company SEPPIC;
MICROPEARL™ LM is a mixture of squalane, poly(methyl methacrylate) and menthol, sold by the company SEPPIC;
SEPICONTROL™ A5 is a mixture of capryloyl glycine, sarcosine, and extract of cinnamon (Cinnamon zylanicum), sold by the company SEPPIC, such as those described in international patent application PCT/FR98/01313 filed on Jun. 23, 1998;

LANOL™ 2681 is a mixture of coconut caprylate/caprate sold by the company SEPPIC;

MONTANOV™ 202 is an APG/fatty alcohol composition as described in WO 98/47610, sold by the company SEPPIC;

PROTEOL™ APL is a foaming surfactant, sold by the company SEPPIC;

SCHERCEMOL™ TISC is an ester (triisostearyl citrate) sold by the company SCHER;

VISTANOL™ NPGC is an ester (neopentyl glycol dicaprate) sold by the company SEWA KASEI;

ANTARON™ V216 is a synthetic polymer (PVP/hexadecene copolymer) distributed by the company UNIVAR;

C MALTIDEX™ H16322 is a polyol (maltitol syrup) sold by the company CERESTAR;

SEPIWHITE™ MSH (INCI name: ω-undecylenoyl phenylalanine) is a skin-lightening agent sold by the company SEPPIC;

DC 345™ is a CYCLOMETHICONE sold by the company DOW CORNING;

DC 5225C™ is a mixture of cyclopentasiloxane and DIMETHICONE copolyol sold by the company DOW CORNING;

SEPICALM™ VG is a soothing activator (sodium palmitoyl proline) sold by the company SEPPIC;

MT100VT is a micronized titanium dioxide that has undergone a surface treatment (aluminum hydroxide/stearic acid) distributed by the company UNIPEX;

Z-COTE HP1™ is a micronized zinc oxide that has undergone a surface treatment, distributed by GATTEFOSSE;

CANDURIN PAPRIKA™ is a mixture of potassium aluminum silicate and iron oxide;

MICROPEARL™ M310 is an ultrafine powder with a very soft feel and a matting action, sold by the company MATSUMO;

PRIMOL™ 352 is a mineral oil sold by the company EXXON;

PECOSIL™ DCT is sodium DIMETHICONE PEG-7 acetyl methyltaurate sold by the company PHOENIX;

PECOSIL™ PS 100 is DIMETHICONE PEG-7 sold by the company PHOENIX;

EFFICACIA™ M is acacia gum sold by the company CNI;

EUXYL™ PE910 is a mixture of phenoxyethanol and ethylhexyl glycerol sold by the company Schülke & Mayr;

GIVOBIO™ GZn (INCI name: zinc gluconate): composition sold by the company SEPPIC;

SEPICALM™ S: (INCI name: sodium cocoyl amino acids and sarcosine and potassium aspartate and magnesium aspartate): anti-inflammatory composition sold by the company SEPPIC;

SOLAGUM™ AX (acacia senegal gum and xanthan gum) is a thickening and stabilizing polymer sold by the company SEPPIC;

EASYNOV™ (INCI name: octyldodecanol, octyldodecyl xyloside and PEG-30 dipolyhydroxystearate) is an emulsifying composition sold by the company SEPPIC;

Fragrance concentrate A: fragrance 61303658 sold by the company Drom;

Fragrance concentrate B: "green water", sold by the company MLW;

AMONYL™ 380 BA is a cocamidopropyl betaine, sold by the company SEPPIC;

ORAMIX™ NS 10 is a foaming composition comprising decylpolyglucoside, dodecylpolyglucoside and tetradecylpolyglucoside, sold by the company SEPPIC;

JAGUAR™ C14 S (INCI name: guar hydroxypropyltrimonium chloride) is a conditioning agent sold by the company Rhodia;

Polyquaternium-7 is a cationic synthetic polymer which is in the form of a quaternary ammonium derivative, and used as a film-forming agent and as an antistatic coating;

Polyquaternium-10 is a hydroxyethylcellulose polymer which is in the form of a quaternized derivative, and used as a thickener;

MONTANOV™ L is an emulsifier sold by the company SEPPIC;

SEPICIDE™ HB (INCI name: phenoxyethanol/methylparaben/ethylparaben/propyl-paraben/butylparaben) is a preservative.

The invention claimed is:

1. A crosslinked anionic polyelectrolyte resulting from the polymerization, for 100 mol %:
   (i) of a proportion greater than or equal to 30 mol % and less than 99.5 mol % of monomer units derived from partially salified or totally salified 2-methyl-2-[(1-oxo-2-proenyl)amino]-1-propanesulfonic acid in sodium salt or ammonium salt form;
   (ii) of a proportion greater than or equal to 0. 5 mol % and less than or equal to 5% of monomer units derived from at least one monomer of formula (I):

$$CH_2\!=\!CH(CH_3)\!-\!C(\!=\!O)\!-\!OR_1 \qquad (I)$$

in which $R_1$ represents an alkyl radical comprising from ten to eighteen carbon atoms, wherein monomer units are derived from: lauryl methacrylate of a formula $(I_1)$ corresponding to formula (I) in which $R_1$ represents a dodecyl radical, and from stearyl methacrylate of formula $(I_2)$ corresponding to formula (I) in which $R_1$ represents an octadecyl radical, in a mole ratio of the monomer units of formula $(I_1)$/ the monomer units of formula $(I_2)$ greater than or equal to 1/10 and less than equal to 10/1;
   (iii) of a proportion greater than 0 mol % and less than or equal to 5 mol % of monomer units derived from at least one diethylene or polyethylene crosslinking monomer; and
   (iv) of a proportion of greater than 0 mol % and less than 69.5 mol % of monomer units derived from a neutral monomer.

2. The crosslinked anionic polyelectrolyte as defined in claim 1, wherein the mole proportion of monomer units derived from at least one diethylene or polyethylene crosslinking monomer is greater than or equal to 0.1 mol % and less than or equal to 3.0 mol %.

3. The crosslinked anionic polyelectrolyte as defined in claim 1, wherein the crosslinking agent and/or the branching agent is selected from the group consisting of ethylene glycol dimethacrylate, tetraallyloxyethane, ethylene glycol diacrylate, diallylurea, triallylamine, trimethylolpropane triacrylate and methylenebis(acrylamide), and a mixture thereof.

4. The anionic polyelectrolyte as defined in claim 1, wherein the anionic polyelectrolyte is obtained by polymerization in the presence of one or more neutral monomers, in a mole proportion of neutral monomer, for 100 mol % of the monomers used, of less than or equal to 30 mol %.

5. The crosslinked anionic polyelectrolyte as defined claim 1, resulting from the polymerization, for 100 mol %:
(i) of a mole proportion greater than or equal to 75 mol % and less than or equal to 95 mol %, of the monomer units derived from partially salified or totally salified 2-methyl-2-[(1-oxo-2-propenyl)amino]-1-propanesulfonic acid in sodium salt or ammonium salt form;
(ii) of a proportion greater than or equal to 0.5 mol % and less than or equal to 5 mol % of monomer units derived from the lauryl methacrylate of formula ($I_1$), and from the stearyl methacrylate of formula ($I_2$), in a mole ratio of the monomer units of formula ($I_1$)/ the monomer units of formula ($I_2$) greater than or equal to 1/6 and less than or equal to 6/1;
(iii) of a proportion greater than or equal to 0.5 mol % and less than or equal to 3.0 mol % of monomer units derived from at least one diethylene or polyethylene crosslinking monomer selected from the group consisting of triallylamine, trimethylolpropane triacrylate and methylenebis(acrylamide); and
(iv) from a mole proportion greater than or equal to 4.0 mol % and less than or equal to 20 mol % of the monomer units derived from a neutral monomer.

6. The crosslinked anionic polyelectrolyte as defined in claim 2, resulting from the polymerization, for 100 mol %:
(i) of a proportion greater than or equal to 83 mol % and less than or equal to 90 mol % of the monomer units derived from partially salified or totally salified 2-methyl-2-[(1-oxo-2-propenyl)amino]-1-propanesulfonic acid in sodium salt or ammonium salt form;
(ii) of a proportion greater than or equal to 1.5 mol % and less than or equal to 2.5 mol % of monomer units derived from the lauryl methacrylate of formula ($I_1$) and from the stearyl methacrylate of formula ($I_2$), in a mole ratio of the monomer units of formula ($I_1$)/ the monomer units of formula ($I_2$) greater than or equal to 1/6 and less than or equal to 6/1;
(iii) of a proportion greater than or equal to 0.5 mol % and less than or equal to 3.0 mol % of monomer units derived from trimethylolpropane triacrylate or methylenebis(acrylamide); and
(iv) of a proportion greater than or equal to 8 mol % to less than or equal to 15 mol % of monomer units derived from (2-hydroxyethyl) acrylate.

7. A cosmetic, dermopharmaceutical or pharmaceutical topical composition comprising the anionic polyelectrolyte as defined in claim 1, as a thickener and/or as a stabilizer and/or as an emulsifier.

8. A topical composition, comprising from 0.1% to 10% by weight of the anionic polyelectrolyte as defined in claim 1.

* * * * *